(12) United States Patent
Quesnel et al.

(10) Patent No.: US 8,822,508 B2
(45) Date of Patent: Sep. 2, 2014

(54) 2-OXO-1-PYRROLIDINYL IMIDAZOTHIADIAZOLE DERIVATIVES

(75) Inventors: Yannick Quesnel, Brussels (BE); Laurent Turet, Brussels (BE); Joël Mercier, Brussels (BE)

(73) Assignee: UCB Pharma, S.A., Brussels (BE)

( * ) Notice: Subject to any disclaimer, the term of this patent is extended or adjusted under 35 U.S.C. 154(b) by 311 days.

(21) Appl. No.: 13/502,546

(22) PCT Filed: Oct. 21, 2010

(86) PCT No.: PCT/EP2010/006434
§ 371 (c)(1),
(2), (4) Date: Jun. 13, 2012

(87) PCT Pub. No.: WO2011/047860
PCT Pub. Date: Apr. 28, 2011

(65) Prior Publication Data
US 2012/0245208 A1 Sep. 27, 2012

(30) Foreign Application Priority Data
Oct. 23, 2009 (EP) ..................................... 09173912

(51) Int. Cl.
*A61K 31/433* (2006.01)
*C07D 513/04* (2006.01)

(52) U.S. Cl.
CPC ................................... *C07D 513/04* (2013.01)
USPC .......................................... 514/363; 548/126

(58) Field of Classification Search
None
See application file for complete search history.

(56) References Cited

U.S. PATENT DOCUMENTS 8,178,533 B2 * 5/2012 Kenda et al. .................. 514/248

FOREIGN PATENT DOCUMENTS

| WO | 01/62726 A2 | 8/2001 |
| WO | 2005/054188 A1 | 6/2005 |
| WO | 2006/128692 A2 | 12/2006 |
| WO | 2006/128693 A2 | 12/2006 |

\* cited by examiner

*Primary Examiner* — Yong Chu
(74) *Attorney, Agent, or Firm* — McDonnell Boehnen Hulbert & Berghoff LLP

(57) ABSTRACT

The present invention relates to 2-oxo-1-pyrrolidine imidazothiadiazole derivatives, processes for preparing them, pharmaceutical compositions containing them and their use as pharmaceuticals.

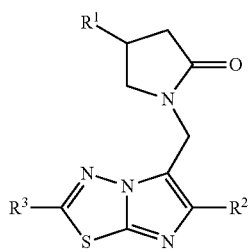

20 Claims, No Drawings

2-OXO-1-PYRROLIDINYL IMIDAZOTHIADIAZOLE DERIVATIVES

This application is a U.S. national phase of International Application No. PCT/EP2010/006434, filed Oct. 21, 2010, the disclosure of which is hereby incorporated by reference in its entirety.

INTRODUCTION

The present invention relates to 2-oxo-1-pyrrolidinyl imidazothiadiazole derivatives, processes for preparing them, pharmaceutical compositions containing them and their use as pharmaceuticals.

European Patent No. 0 162 036 B1 discloses compound (S)-α-ethyl-2-oxo-1-pyrrolidine acetamide, which is known under the International Nonproprietary Name (INN) levetiracetam.

Levetiracetam, a laevorotary compound, is disclosed as a protective agent for the treatment and prevention of hypoxic and ischemic type aggressions of the central nervous system. This compound is also effective in the treatment of epilepsy (seizure control), a therapeutic indication for which it has been demonstrated that its dextrorotatory enantiomer (R)-α-ethyl-2-oxo-1-pyrrolidine acetamide, also known from European Patent No. 0 165 919 B1, completely lacks activity (Gower A. J. et at., Eur. J. Pharmacol. (1992), 222, 193-203).

A persistent problem in seizure control arises with those patients who do not at all or only insufficiently respond to currently available treatments. Those patients are viewed as being refractory to treatment and represent a considerable challenge for the medical community. It is estimated that about 30% of epilepsy patients are to be classified as being refractory. Hence, there is a need to develop new medications that specifically target this population of patients.

Belavin I. Yu. et al. (Khimiko-Farmatsevticheskii Zhurnal (1992), 26 (9-10), 74-76) discloses 1-[1-(1H-benzimidazol-1-yl)ethyl]-2-pyrrolidinone and its anticonvulsant activity.

WO 01/62726 discloses pyrrolidinone compounds having the following formula:

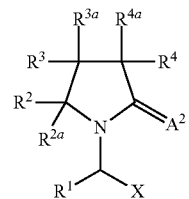

WO 2005/054188 discloses imidazole derivatives having the following formula:

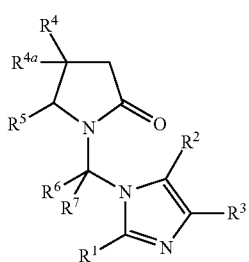

The imidazole or benzimidazole is attached by a nitrogen to the methylene linker of the pyrrolidinone.

WO 2006/128693 discloses pyrrolidinone compounds of the following formula (A)

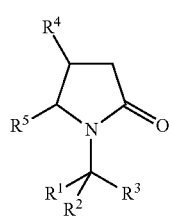

wherein
R$^1$ is hydrogen, substituted or unsubstituted C$_{1-12}$ alkyl, substituted or unsubstituted aryl or substituted or unsubstituted 3-8 membered heterocycle.
R$^2$ is hydrogen. Alternatively, R$^1$ and R$^2$ may be linked together in such a way to form a C$_{3-6}$ cycloalkyl.
R$^3$ is either
 (a) a substituted or unsubstituted heterocycle linked to the rest of the molecule via one of its C atoms, said heterocycle is selected from the group consisting of:
   1H-benzimidazol-6-yl;
   1H-benzimidazol-7-yl;
   imidazo[1,2-a]pyridin-3-yl;
   imidazo[1,2-a]pyrimidin-3-yl;
   imidazo[1,2-b][1,2,4]triazin-7-yl;
   imidazo[1,2-b]pyridazin-3-yl;
   5,6,7,8-tetrahydroimidazo[1,2-b]pyridazin-3-yl;
   imidazo[2,1-b][1,3,4]thiadiazol-5-yl;
   imidazo[2,1-b][1,3]thiazol-5-yl;
   3H-imidazo[4,5-b]pyridin-7-yl;
   1H-imidazol-4-yl;
   1H-imidazol-5-yl;
   1H-indol-2-yl;
   1H-indol-3-yl;
   1H-indol-4-yl;
   1H-indol-7-yl;
   isoxazol-4-yl;
   1H-pyrazol-4-yl;
   1H-pyrazol-5-yl;
   1H-pyrazolo[1,5-a]pyrimidin-3-yl;
   1H-pyrazolo[3,4-b]pyridin-3-yl;
   pyridazin-4-yl;
   pyridin-2-yl;
   pyridin-3-yl;
   pyridin-4-yl;
   1H-pyrrolo[2,3-b]pyridin-3-yl;
   1H-pyrrolo[2,3-b]pyridin-4-yl;
   1H-pyrrolo[2,3-b]pyridin-5-yl;
   1H-pyrrolo[2,3-c]pyridin-2-yl;
   1H-pyrrolo[2,3-c]pyridin-3-yl;
   1H-pyrrolo[3,2-b]pyridin-3-yl;
   1H-pyrrolo[3,2-c]pyridin-2-yl;
   1H-pyrrolo[3,2-c]pyridin-3-yl;
   1,3,4-thiadiazol-2-yl;
   1,3-thiazol-5-yl;
   [1,2,4]triazolo[4,3-b]pyridazin-7-yl;
   [1,2,4]triazolo[4,3-b]pyridazin-8-yl;
   indolizin-3-yl;
or alternatively R$^3$ is
 (b) a substituted or unsubstituted heterocycle linked to the rest of the molecule via one of its N atoms, said heterocycle is selected from the group consisting of:
   1H-1,2,3-benzotriazol-1-yl;
   1H-imidazo[4,5-b]pyridin-1-yl;
   3H-imidazo[4,5-b]pyridin-3-yl;

7H-imidazo[4,5-c]pyridazin-7-yl;
1H-indol-1-yl;
2,3-dihydro-1H-indol-1-yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-pyrrol-1-yl;
2-chloro-1H-benzimidazol-1-yl.

$R^4$ in formula (I) is selected from the group comprising or consisting of hydrogen; $C_{1-12}$ alkyl optionally substituted by halogen, $C_{1-4}$ alkoxy, $C_{1-4}$ alkylthio, azido, nitrooxy or an aryl; $C_{2-12}$ alkenyl optionally substituted by halogen; $C_{2-12}$ alkynyl optionally substituted by halogen; azido; alkoxycarbonylamino; arylsulfonyloxy; a substituted or unsubstituted aryl; or a 3-8 membered substituted or unsubstituted heterocycle.

The compounds of WO 2006/128693 are said to be useful in the treatment of epilepsy, epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless legs syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

SUMMARY OF THE INVENTION

The invention provides new 2-oxo-1-pyrrolidinyl imidazothiadiazole derivatives having the formula I, their geometrical isomers, enantiomers, diastereoisomers and mixtures, or a pharmaceutically acceptable salt thereof,

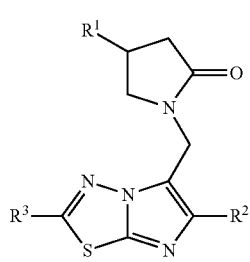

Further aspects of the invention will become apparent from the detailed description.

DETAILED DESCRIPTION OF THE INVENTION

The present invention relates to 2-oxo-1-pyrrolidinyl imidazothiadiazole derivatives according to formula I,

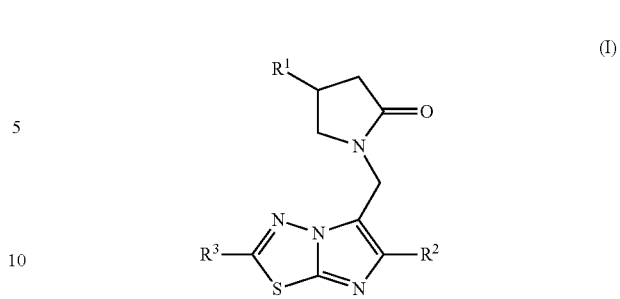

wherein
$R^1$ is a $C_{1-4}$ alkyl containing at least one halogen substituent.
$R^2$ is either a halogen (chlorine, bromine, iodine) or a $C_{1-4}$ alkyl containing at least one halogen substituent.
$R^3$ is a $C_{1-4}$ alkyl (e.g. a methyl or ethyl) containing at least one hydroxy (OH) or an alkoxy (e.g. methoxy or ethoxy or propoxy) substituent.

Also comprised are tautomers, geometrical isomers, enantiomers, diastereomers and mixtures, or a pharmaceutically acceptable salt of compounds of formula I. The molecules of the present invention may be deuterated at any position.

In a specific embodiment, $R^1$ is a 2,2-difluoropropyl, a 2-chloro-2,2-difluoroethyl, a 2,2-difluoroethyl, a 2,2,2-trifluoroethyl, a 3,3,3-trifluoropropyl or a 2-fluoroethyl moiety, preferably a 2,2-difluoropropyl, a 2-chloro-2,2-difluoroethyl, a 2,2,2-trifluoroethyl or a 3,3,3-trifluoropropyl group.

In a further specific embodiment, $R^2$ is either a chloro, a difluoromethyl or a trifluoro-methyl moiety.

In a further specific embodiment, $R^3$ is either a hydroxymethyl, a methoxymethyl, a [($^2H_3$)methyloxy]methyl, a methoxy($^2H_2$)methyl, a (2,2,2-trifluoroethoxy)methyl or a 2-methoxyethyl moiety, preferably a methoxymethyl moiety.

In a further specific embodiment compounds of formula I are those wherein:
$R^1$ is a 2,2-difluoropropyl, a 2-chloro-2,2-difluoroethyl, a 2,2,2-trifluoroethyl or a 3,3,3-trifluoropropyl moiety;
$R^2$ is a chloro, a difluoromethyl or a trifluoromethyl moiety;
$R^3$ is a methoxymethyl moiety.

Specific compounds of the present invention are those selected from the group consisting of:
4-(2,2-difluoropropyl)-1-{[2-(methoxymethyl)-6-(trifluoromethyl)imidazo[2,1-b][1,3,4]thiadiazol-5-yl]methyl}pyrrolidin-2-one;
(+)-4-(2,2-difluoropropyl)-1-{[2-(methoxymethyl)-6-(trifluoromethyl)imidazo[2,1-b][1,3,4]thiadiazol-5-yl]methyl}pyrrolidin-2-one;
(−)-4-(2,2-difluoropropyl)-1-{[2-(methoxymethyl)-6-(trifluoromethyl)imidazo[2,1-b][1,3,4]thiadiazol-5-yl]methyl}pyrrolidin-2-one;
4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one trifluoroacetate;
(4S)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one;
(4R)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one;
4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one;

(4R)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one;

(4S)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one;

1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one;

(4R)-1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one;

(4S)-1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one;

1-{[2-(hydroxymethyl)-6-(trifluoromethyl)imidazo[2,1-b][1,3,4]thiadiazol-5-yl]methyl}-4-(2,2,2-trifluoroethyl)pyrrolidin-2-one;

1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one;

(4S)-1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one;

(4R)-1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one;

(4S)-1-{[2-(hydroxymethyl)-6-(trifluoromethyl)imidazo[2,1-b][1,3,4]thiadiazol-5-yl]methyl}-4-(3,3,3-trifluoropropyl)pyrrolidin-2-one;

4-(2,2-difluoroethyl)-1-{[2-(methoxymethyl)-6-(trifluoromethyl)imidazo[2,1-b][1,3,4]thiadiazol-5-yl]methyl}pyrrolidin-2-one;

(+)-4-(2,2-difluoroethyl)-1-{[2-(methoxymethyl)-6-(trifluoromethyl)imidazo[2,1-b][1,3,4]thiadiazol-5-yl]methyl}pyrrolidin-2-one;

(−)-4-(2,2-difluoroethyl)-1-{[2-(methoxymethyl)-6-(trifluoromethyl)imidazo[2,1-b][1,3,4]thiadiazol-5-yl]methyl}pyrrolidin-2-one;

4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one;

(−)-4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one;

(+)-4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one;

4-(2-chloro-2,2-difluoroethyl)-1-({6-chloro-2-[(2,2,2-trifluoroethoxy)methyl]imidazo[2,1-b][1,3,4]thiadiazol-5-yl}methyl)pyrrolidin-2-one;

1-{[6-chloro-2-(methoxymethyl)imidazo[2,1-b][1,3,4]thiadiazol-5-yl]methyl}-4-(3,3,3-trifluoropropyl)pyrrolidin-2-one;

(−)-1-{[6-chloro-2-(methoxymethyl)imidazo[2,1-b][1,3,4]thiadiazol-5-yl]methyl}-4-(3,3,3-trifluoropropyl)pyrrolidin-2-one;

(+)-1-{[6-chloro-2-(methoxymethyl)imidazo[2,1-b][1,3,4]thiadiazol-5-yl]methyl}-4-(3,3,3-trifluoropropyl)pyrrolidin-2-one;

1-{[6-chloro-2-(methoxymethyl)imidazo[2,1-b][1,3,4]thiadiazol-5-yl]methyl}-4-(2-fluoroethyl)pyrrolidin-2-one;

(4R)-1-{[2-(hydroxymethyl)-6-(trifluoromethyl)imidazo[2,1-b][1,3,4]thiadiazol-5-yl]methyl}-4-(2,2,2-trifluoroethyl)pyrrolidin-2-one;

(4R)-4-(2-chloro-2,2-difluoroethyl)-1-{[2-{[($^2$H$_3$)methyloxy]methyl}-6-(trifluoromethyl)imidazo[2,1-b][1,3,4]thiadiazol-5-yl]methyl}pyrrolidin-2-one;

(4R)-4-(2-chloro-2,2-difluoroethyl)-1-({2-[methoxy($^2$H$_2$)methyl]-6-(trifluoromethyl)imidazo[2,1-b][1,3,4]thiadiazol-5-yl}methyl)pyrrolidin-2-one;

(4R)-4-(2-chloro-2,2-difluoroethyl)-1-{[2-(methoxymethyl)-6-(trifluoromethyl)imidazo[2,1-b][1,3,4]thiadiazol-5-yl]($^2$H$_2$)methyl}pyrrolidin-2-one 4-(2-chloro-2,2-difluoroethyl)-1-{[2-(2-methoxyethyl)-6-(trifluoromethyl)imidazo[2,1-b][1,3,4]thiadiazol-5-yl]methyl}pyrrolidin-2-one;

1-{[2-(2-methoxyethyl)-6-(trifluoromethyl)imidazo[2,1-b][1,3,4]thiadiazol-5-yl]methyl}-4-(2,2,2-trifluoroethyl)pyrrolidin-2-one; and 1-([2-(2-methoxyethyl)-6-(trifluoromethyl)imidazo[2,1-b][1,3,4]thiadiazol-5-yl]methyl)-4-(3,3,3-trifluoropropyl)pyrrolidin-2-one.

The following paragraphs provide definitions of the various chemical moieties that make up the compounds according to the invention and are intended to apply uniformly throughout the specification and claims unless an otherwise expressly set out definition provides a broader definition.

"$C_{1-4}$ alkyl" refers to alkyl groups having 1 to 4 carbon atoms. This term is exemplified by groups such as methyl, ethyl, n-propyl, isopropyl, n-butyl, isobutyl, tert-butyl. "$C_{1-4}$ alkyl" groups may be substituted by one or more substituents selected from halogen, hydroxy or alkoxy.

Any moiety "H" in formula I may be the isotope hydrogen, deuterium or tritium.

"Hydroxy" represents a group of formula —OH.

"Alkoxy" refers to the group —O—R where R includes "$C_{1-4}$ alkyl".

"Halogen" refers to fluoro, chloro, bromo and iodo atoms, preferably fluoro and chloro.

The "pharmaceutically acceptable salts" according to the invention include therapeutically active, non-toxic acid or base salt forms which the compounds of formula I are able to form.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

The expression "enantiomerically pure" as used herein refers to compounds which have enantiomeric excess (ee) greater than 95%.

Compounds according to the present invention may exist in different polymorphic forms. Although not explicitly indicated in the above formula, such forms are intended to be included within the scope of the present invention.

The compounds of formula I according to the invention can be prepared analogously to conventional methods as understood by the person skilled in the art of synthetic organic chemistry.

According to one embodiment, compounds having the general formula I may be prepared by reaction of a compound of formula II with an heterocycle of formula III according to the equation:

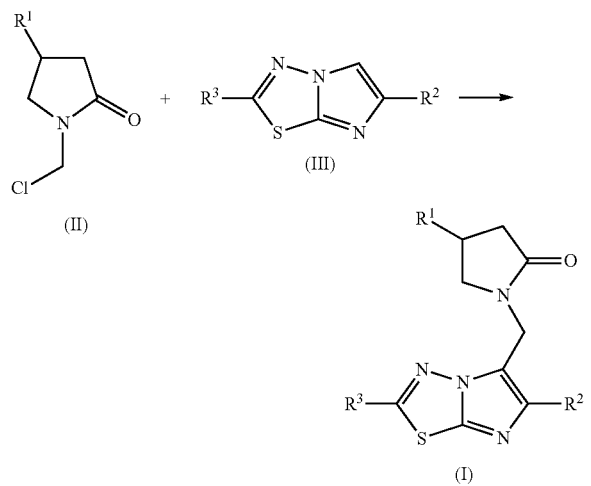

wherein $R^1$, $R^2$ and $R^3$ have the same definitions as defined above for compounds of formula I.

This reaction may be performed in dioxane in the presence of a lewis acid such as $AlCl_3$ or $ZnCl_2$, at a temperature ranging from 20° C. to 100° C., or according to any method known to the person skilled in the art.

Compounds of formula II may be prepared from the corresponding pyrrolidones of formula IV according to the methods described in PCT patent application WO2006/128693 or according to any other method known to the person skilled in the art.

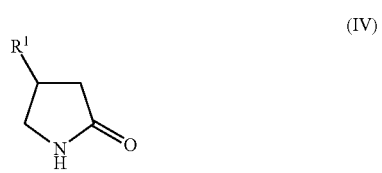

The synthesis of compounds of formula IV can be performed using procedures described in the literature or known to the person skilled in the art.

Compounds of formula III wherein $R^2$ is $C_{1-4}$ alkyl may be performed by reaction of a compound of formula V with a bromo derivative of formula VI according to the equation

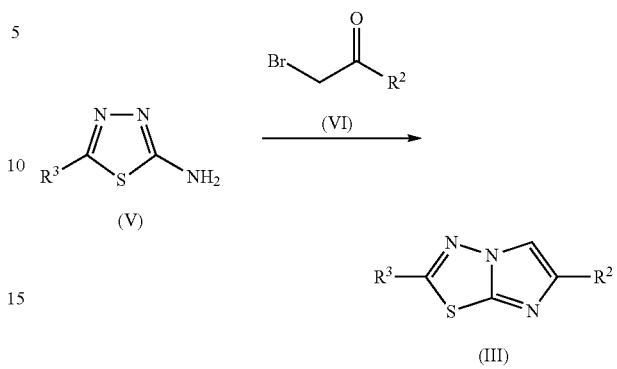

wherein $R^2$ is $C_{1-4}$ alkyl and $R^3$ has the same definition as described above for compounds of formula I. This reaction can be performed using procedures described in the literature or known to the person skilled in the art.

Compounds of formula III wherein $R^2$ is Cl may be prepared by cyclisation of a compound of formula VII according to the equation

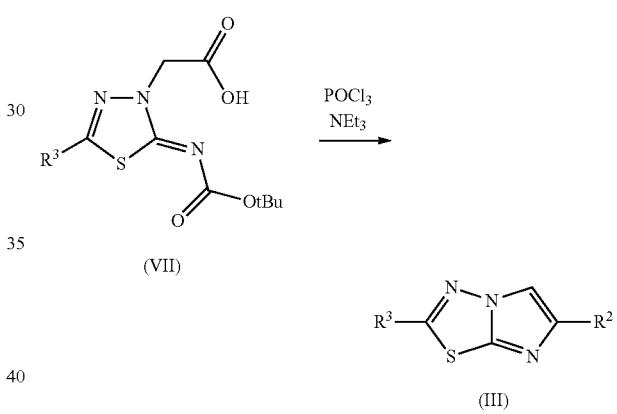

wherein $R^2$ is Cl and $R^3$ has the same definition as described above for compounds of formula I.

This reaction can be performed by treatment of a compound of formula VII with a halogenating agent such as phosphorus oxychloride with a tertiary amine such as triethylamine in classical organic solvent such as acetonitrile, or according to any other method known by the person skilled in the art.

Compound of formula VII can be prepared by protection of its amino group by a Boc group, then by reaction of the resulting intermediate with a bromo derivative of formula VI wherein R2 is OH, according to the equation

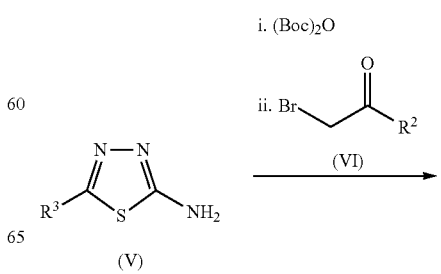

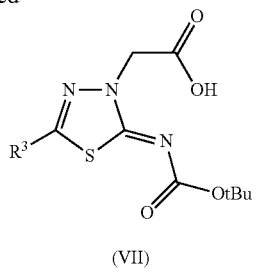

(VII)

This reaction may be performed using procedures described in the literature or known to the person skilled in the art.

According to another embodiment, variations on the $R^1$ lateral chains of compounds of formula I may be performed according to any method known to the person skilled in the art.

In another embodiment, the present invention includes the synthesis of the following intermediates:
3-(aminomethyl)-5-chloro-5,5-difluoropentanoic acid;
methyl 3-(aminomethyl)-5-chloro-5,5-difluoropentanoate;
4-(2-chloro-2,2-difluoroethyl)-1-(chloromethyl)pyrrolidin-2-one;
(4R)-4-(2-chloro-2,2-difluoroethyl)-1-(chloromethyl)pyrrolidin-2-one;
(4R)-4-(2,2,2-trifluoroethyl)pyrrolidin-2-one;
ethyl 6,6,6-trifluoro-3-(nitromethyl)hexanoate;
4-(3,3,3-trifluoropropyl)pyrrolidin-2-one;
(4S)-4-(3,3,3-trifluoropropyl)pyrrolidin-2-one;
4-(2,2-difluoropropyl)pyrrolidin-2-one;
4-[2-(benzyloxy)ethyl]pyrrolidin-2-one;
4-(2,2-difluoroethyl)pyrrolidin-2-one;
4-(2-chloro-2,2-difluoroethyl)-1-(hydroxymethyl)pyrrolidin-2-one;
(4R)-4-(2-chloro-2,2-difluoroethyl)-1-(hydroxymethyl)pyrrolidin-2-one;
1-(hydroxymethyl)-4-(2,2,2-trifluoroethyl)pyrrolidin-2-one;
(4R)-1-(hydroxymethyl)-4-(2,2,2-trifluoroethyl)pyrrolidin-2-one;
1-(hydroxymethyl)-4-(3,3,3-trifluoropropyl)pyrrolidin-2-one;
(4S)-1-(hydroxymethyl)-4-(3,3,3-trifluoropropyl)pyrrolidin-2-one;
4-(2,2-difluoropropyl)-1-(hydroxymethyl)pyrrolidin-2-one;
4-[2-(benzyloxy)ethyl]-1-(hydroxymethyl)pyrrolidin-2-one;
4-(2,2-difluoroethyl)-1-(hydroxymethyl)pyrrolidin-2-one;
4-(2-chloro-2,2-difluoroethyl)-1-(chloromethyl)pyrrolidin-2-one;
(4R)-4-(2-chloro-2,2-difluoroethyl)-1-(chloromethyl)pyrrolidin-2-one;
1-(chloromethyl)-4-(2,2,2-trifluoroethyl)pyrrolidin-2-one;
(4R)-1-(chloromethyl)-4-(2,2,2-trifluoroethyl)pyrrolidin-2-one;
1-(chloromethyl)-4-(3,3,3-trifluoropropyl)pyrrolidin-2-one;
(4S)-1-(chloromethyl)-4-(3,3,3-trifluoropropyl)pyrrolidin-2-one;
1-(chloromethyl)-4-(2,2-difluoropropyl)pyrrolidin-2-one;
4-[2-(benzyloxy)ethyl]-1-(chloromethyl)pyrrolidin-2-one;
1-(chloromethyl)-4-(2,2-difluoroethyl)pyrrolidin-2-one;
5-[(benzyloxy)methyl]-1,3,4-thiadiazol-2-amine;
5-[(2,2,2-trifluoroethoxy)methyl]-1,3,4-thiadiazol-2-amine;
2-(methoxymethyl)-6-(trifluoromethyl)imidazo[2,1-b][1,3,4]thiadiazole;
2-[(benzyloxy)methyl]-6-(trifluoromethyl)imidazo[2,1-b][1,3,4]thiadiazole;
6-(difluoromethyl)-2-(methoxymethyl)imidazo[2,1-b][1,3,4]thiadiazole;
2-(2-methoxyethyl)-6-(trifluoromethyl)imidazo[2,1-b][1,3,4]thiadiazole;
tert-butyl [5-(methoxymethyl)-1,3,4-thiadiazol-2-yl]carbamate;
tert-butyl {5-[(2,2,2-trifluoroethoxy)methyl]-1,3,4-thiadiazol-2-yl}carbamate;
{2-[(tert-butoxycarbonyl)imino]-5-(methoxymethyl)-1,3,4-thiadiazol-3(2H)-yl}acetic acid;
{2-[(tert-butoxycarbonyl)imino]-5-[(2,2,2-trifluoroethoxy)methyl]-1,3,4-thiadiazol-3(2H)-yl}acetic acid;
6-chloro-2-(methoxymethyl)imidazo[2,1-b][1,3,4]thiadiazole;
6-chloro-2-[(2,2,2-trifluoroethoxy)methyl]imidazo[2,1-b][1,3,4]thiadiazole;
4-[2-(benzyloxy)ethyl]-1-{[6-chloro-2-(methoxymethyl)imidazo[2,1-b][1,3,4]thiadiazol-5-yl]methyl}pyrrolidin-2-one;
1-{[6-chloro-2-(methoxymethyl)imidazo[2,1-b][1,3,4]thiadiazol-5-yl]methyl}-4-(2-hydroxyethyl)pyrrolidin-2-one;
2-(1-{[6-chloro-2-(methoxymethyl)imidazo[2,1-b][1,3,4]thiadiazol-5-yl]methyl}-5-oxopyrrolidin-3-yl)ethyl 4-methylbenzenesulfonate;
ethyl 6-(trifluoromethyl)imidazo[2,1-b][1,3,4]thiadiazole-2-carboxylate;
[6-(trifluoromethyl)imidazo[2,1-b][1,3,4]thiadiazol-2-yl]($^2H_2$)methanol;
2-[methoxy($^2H_2$)methyl]-6-(trifluoromethyl)imidazo[2,1-b][1,3,4]thiadiazole;
(4R)-4-(2-chloro-2,2-difluoroethyl)-1-[hydroxy($^2H_2$)methyl]pyrrolidin-2-one; and
(4R)-4-(2-chloro-2,2-difluoroethyl)-1-[chloro($^2H_2$)methyl]pyrrolidin-2-one.

The compounds of the present invention are for use as a medicament, in the treatment of epilepsy, epileptogenesis, seizure disorders, convulsions, in particular for refractory seizures.

Seizures can be classified as refractory when a patient fails to achieve seizure freedom for 12 months or more of state of the art treatment with two or more anti-epileptic drugs at maximal tolerated doses.

The methods of the invention comprise administration to a mammal (preferably a human) suffering from above mentioned conditions or disorders, of a compound according to the invention in an amount sufficient to alleviate or prevent the disorder or condition.

The compound is conveniently administered in any suitable unit dosage form, including but not limited to one containing 1 to 2000 mg, preferably 1 to 1000 mg, more preferably 1 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manifestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

A further aspect of the present invention relates to a pharmaceutical composition comprising an effective amount of a compound of formula I in combination with a pharmaceutically acceptable diluent or carrier.

Activity in any of the above-mentioned indications can of course be determined by carrying out suitable clinical trials in a manner known to a person skilled in the relevant art for the particular indication and/or in the design of clinical trials in general.

For treating diseases, compounds of formula I or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula I or a pharmaceutically acceptable salt thereof in combination with a pharmaceutically acceptable diluent or carrier.

To prepare a pharmaceutical composition according to the invention, one or more of the compounds of formula I or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner.

Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula I in compositions for oral administration is at least 0.5% by weight and can be up to 80% by weight with respect to the total weight of the composition.

In accordance with the invention it has also been found that the compounds of formula I or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenyloin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, $\beta$-blockers, antiarrhythmics, triptans, ergot derivatives and amantadine.

For oral compositions, the daily dosage is in the range 1 mg to 2000 mg of compounds of formula I. For oral compositions the dosage unit is in the range 1 mg to 1000 mg of compounds of formula I, preferably 1 mg to 500 mg.

In compositions for parenteral administration, the quantity of compound of formula I present is at least 0.5% by weight and can be up to 33% by weight with respect to the total weight of the composition. For the preferred parenteral compositions, the dosage unit is in the range 1 mg to 2000 mg of compounds of formula I.

The daily dose can fall within a wide range of dosage units of compound of formula I and is generally in the range 1 to 2000 mg, preferably 1 to 1000 mg. However, it should be understood that the specific doses can be adapted to particular cases depending on the individual requirements, at the physician's discretion.

The SV2 proteins binding compounds provided by this invention and labeled derivatives thereof may be useful as standards and reagents in determining the ability of tested compounds (e.g., a potential pharmaceutical) to bind to the SV2 proteins.

Labeled derivatives of SV2 proteins' ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A and SV2C, but including SV2B, to a putative agent and incubating the membranes or proteins or fragments and the agent with labelled compound of formula I. The method further comprises determining if the binding of the compound of formula I to the protein is inhibited by the putative agent, thereby identifying binding partners for the protein. Thus, the screening assays enable the identification of new drugs or compounds that interact with SV2 proteins. The present invention also provides photoactivable ligands of SV2 proteins.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3H$, a fluorescent label, an enzyme, europium, biotin and other conventional labels for assays of this type.

Labelled compounds of formula I are useful in the methods as probes in assays to screen for new compounds or agents that bind to the SV2 proteins (SV2A, SV2B and SV2C). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly. Possibilities for direct labelling include label groups such as: radiolabels including, but not limited to, $[^3H]$, $[^{14}C]$, $[^{32}P]$, $[^{35}S]$ or $[^{125}I]$, enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of anti-ligand antibodies. The compounds may also include spacers or linkers in cases where the compounds are to be attached to a solid support. To identify agents or compounds which compete or interact with labelled ligands according to the invention for binding to the SV2 proteins (especially SV2A and SV2C), intact cells, cellular or membrane fragments containing SV2A or SV2C or the entire SV2 protein or a fragment thereof can be used. The agent or compound may be incubated with the cells, membranes, SV2 protein or fragment prior to, at the same time as, or after incubation with labelled levetiracetam or an analog or derivative thereof. Assays may be modified or prepared in any available format, including high-throughput screening (HTS) assays that monitor the binding of levetiracetam or the binding of derivatives or analogs thereof to SV2 proteins or fragments thereof. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labeled ligand according to the invention to SV2 or a fragment of SV2 or of labelled levetiracetam, or derivatives or analogs thereof, to SV2 or a fragment of SV2 protein. The inhibition of complex formation may be detected by a variety of techniques such as filtration assays, Flashplates (Perkin Elmer), scintillation proximity assays (SPA, GE). For high-throughput screenings (HTS), scintillation proximity assay which uses microspheres coated with biological membranes or flashplates coated with biological membranes are powerful methods that do not require separation or washing steps.

EXAMPLES

The following examples illustrate how the compounds covered by formula I may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

NMR spectra are recorded on a BRUKER AVANCE 400 NMR Spectrometer fitted with a Linux workstation running XWIN NMR 3.5 software and a 5 mm inverse $^1H$/BB probehead, or BRUKER DRX 400 NMR fitted with a SG Fuel running XWIN NMR 2.6 software and a 5 mm inverse geometry $^1H/^{13}C/^{19}F$ triple probehead. The compound is studied in $d_6$-dimethylsulfoxide (or $d_3$-chloroform) solution at a probe temperature of 313 K or 300 K and at a concentration of 10 mg/ml. The instrument is locked on the deuterium signal of $d_6$-dimethylsulfoxide (or $d_3$-chloroform). Chemical shifts are given in ppm downfield from TMS (tetramethylsilane) taken as internal standard.

HPLC analyses are performed using one of the following systems:
an Agilent 1100 series HPLC system mounted with an INERTSIL ODS 3 C18, DP 5 µm, 250×4.6 mm column. The gradient runs from 100% solvent A (acetonitrile, water, phosphoric acid (5/95/0.001, v/v/v)) to 100% solvent B (acetonitrile, water, phosphoric acid (95/5/0.001, v/v/v)) in 6 min with a hold at 100% B of 4 min. The flow rate is set at 2.5 ml/min. The chromatography is carried out at 35° C.
a HP 1090 series HPLC system mounted with a HPLC Waters Symetry C18, 250×4.6 mm column. The gradient runs from 100% solvent A (methanol, water, phosphoric acid (15/85/0.001M, v/v/M)) to 100% solvent B (methanol, water, phosphoric acid (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:
HPLC Conditions
Analyses are performed using a WATERS Alliance HPLC system mounted with an INERTSIL ODS 3, DP 5 µm, 250× 4.6 mm column.

The gradient runs from 100% solvent A (acetonitrile, water, trifluoroacetic acid (10/90/0.1, v/v/v)) to 100% solvent B (acetonitrile, water, trifluoroacetic acid (90/10/0.1, v/v/v)) in 7 min with a hold at 100% B of 4 min. The flow rate is set at 2.5 ml/min and a split of 1/25 is used just before API source.
MS conditions
Samples are dissolved in acetonitrile/water, 70/30, v/v at the concentration of about 250 µg/ml. API spectra (+ or −) are performed using a FINNIGAN LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN TSQ 700 tandem quadrupole mass spectrometer. The source temperature is set at 150° C.

Mass spectrometric measurements on a TSQ 700 tandem quadrupole mass spectrometer (Finnigan MAT) in GC/MS mode are performed with a gas chromatograph model 3400 (Varian) fitted with a split/splitless injector and a DB-5MS fused-silica column (15 m×0.25 mm I.D., 1 μm) from J&W Scientific. Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

High resolution mass spectrometry measurements are run on a Waters LCT Time of flight mass spectrometer equipped with an ESI source and a Waters Acquity HPLC (column: BEH C18 (1.7 μm, 2.1×50 mm)) with diode array detector. The gradient runs from 98% solvent A (aqueous ammonium formate (63 mg/l), 30% aqueous ammonia (50 μl/l)) to 95% acetonitrile and back in 6 min. The source parameters are as follows: ESI capillary voltage 2.5 kV, cone voltage 135 V, source block temperature 135° C., desolvation temperature 350° C., cone gas flow 20 UHr (Nitrogen), desolvation Gas flow 800 UHr. The detector is set with a flight tube at 7.2 KV and an MCP detector at 2,500 V. Specific rotation is recorded on a Perkin-Elmer 341 polarimeter. The angle of rotation is recorded at 25° C. on 1% solutions in methanol, at 589 nm.

Melting points are determined on a Büch 535 or 545 Tottoli-type fusionometre, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures. Reverse phase separations are carried out using 500 g of either Kromasil C18 10 μm silicagel (acidic or neutral conditions) or Phenomenex Gemini C18 10 μM (basic conditions) in 8-cm ID columns with a flow rate of 150 ml/min. Products are detected at 215 nm unless otherwise specified.

Preparative Chiral Chromatographic separations are performed on a DAICEL Chiralpak AD 20 μm, 100*500 mm column or on a Phenomenex cellulose Lux-2, 250*4.6 mm column using an in-house build instrument with various mixtures of lower alcohols and C5 to C8 linear, branched or cyclic alkanes at±350 ml/min. Solvent mixtures as described in individual procedures.

Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling).

Example 1

Synthesis of 4-substituted 1-(chloromethyl)pyrrolidin-2-one derivatives 1.1 Synthesis of 4-substituted pyrrolidones 1.1.1 Synthesis of 4-(2-chloro-2,2-difluoroethyl)-1-(chloromethyl)pyrrolidin-2-one a4

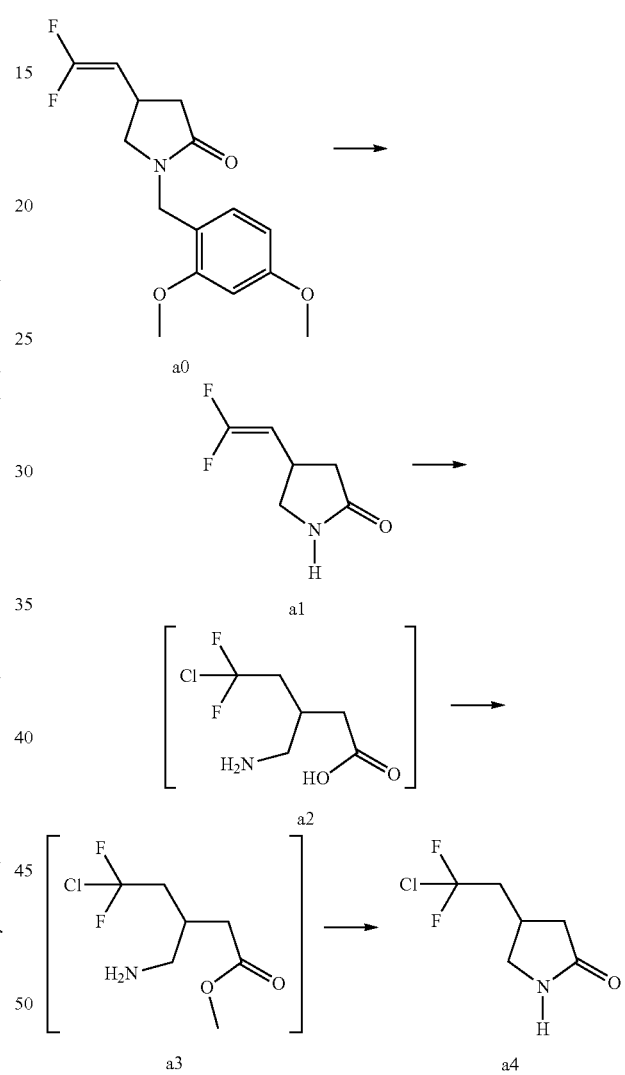

4-(2,2-difluoroethenyl)-1-(2,4-dimethoxybenzyl)pyrrolidin-2-one a0 (50 g) is dissolved in acetic acid (4 vol.) and 37% hydrochloric acid (1 vol.) and the mixture is heated at 90° C. for 4 hours. After cooling, 4-(2,2-difluoroethenyl)pyrrolidin-2-one a1 crashes out and is filtered off the reaction mixture. This intermediate a1 is taken up in 37% hydrochloric acid (5 vol.) and the resulting reaction mixture is heated to 75° C. during 5 days to afford the opened ring a2 as the major compound (LC-MS (MH$^+$): 202/204). This reaction mixture is then evaporated and dried by stripping twice with toluene. The resulting crude oil is dissolved in methanol (6 vol.) and SOCl$_2$ (1.2 mol eq) is added at 2-7° C. After overnight stirring at room temperature, the reaction mixture is evaporated to dryness to afford crude methyl 3-(aminomethyl)-5-chloro-5,5-difluoropentanoate a3 as an oil. This crude oil is dissolved in methanol (4 vol.) and diisopropylethylamine (~1.5 mol eq) is added until pH=9. Reaction mixture is heated at 60° C. during 4 hours to complete the cyclization. Work-up by evaporation of methanol followed by addition of aqueous 2M sodium hydroxyde (6 vol.) is followed by extraction by dichloromethane. The cumulated dichloromethane organic layers are back washed with fractions of 0.5M HCl until pH is slightly acidic to remove traces of DIPEA in the final compound. 4-(2-chloro-2,2-difluoroethyl)-1-(chloromethyl)pyrrolidin-2-one a4 is obtained after solvent removal under reduced pressure and used directly in the next without any further purification.

Yield: 66%.

LC-MS (MH$^+$): 184/186.

(4R)-4-(2-chloro-2,2-difluoroethyl)-1-(chloromethyl)pyrrolidin-2-one a4R is obtained by separation by chiral chromatography of 4-(2-chloro-2,2-difluoroethyl)-1-(chloromethyl)pyrrolidin-2-one a4 (phase: Chiralpak AD-H; 30° C.; column: 100*500 mm; eluent: MeOH/EtOH/iso-hexane/diethylamine 8:2:90:0.1; 300 ml/min).

1.1.2 Synthesis of (4R)-4-(2,2,2-trifluoroethyl)pyrrolidin-2-one a5R (4R)-4-(2,2,2-trifluoroethyl)pyrrolidin-2-one a5R is obtained by separation by chiral chromatography of 4-(2,2,2-trifluoroethyl)pyrrolidin-2-one a5 (phase: Phenomenex cellulose Lux-2; 30° C.; column: 250*4.6 mm; eluent: n-PrOH/iso-hexane/diethylamine 50:50:0.1; 1 ml/min.).

LC-MS (MH$^+$): 168.

1.1.3 Synthesis of 4-(3,3,3-trifluoropropyl)pyrrolidin-2-one a8

To ethyl 6,6,6-trifluorohex-2-enoate a6 (54.42 g, 0.277 mol, 1 eq) in nitromethane (250 ml) is added in one portion 1,8-diazabicyclo[5.4.0]undec-7-ene (DBU, 41.5 ml, 0.277 mol, 1 eq). The reaction mixture is stirred at room temperature for 3 hours, then the nitromethane layer is washed two times a 2N HCl aqueous solution (250 ml). The cumulated aqueous layers are extracted by ethyl acetate (2×250 ml). The cumulated organic layers are dried over MgSO$_4$, filtered and condensed under vacuum to yield 50 g of crude ethyl 6,6,6-trifluoro-3-(nitromethyl)hexanoate a7 which is used in the next step without any further purification.

LC-MS (MH$^+$): 258.

A mixture of crude ethyl 6,6,6-trifluoro-3-(nitromethyl) hexanoate a7 (50 g), Raney Nickel (570 mg, 9.7 mmol, 0.05 eq) and Vanadium metavanadate (227 mg, 2 mmol, 0.01 eq) in ethanol (1 l) is placed in an autoclave under hydrogen pressure (50 bars) at 50° C. for 40 h. After cooling, filtration over celite and condensation under vacuum, 4-(3,3,3-trifluoropropyl)pyrrolidin-2-one a8 (34.3 g) is isolated.

Yield: 68.4%.

LC-MS (MH$^+$): 182.

The following compounds may be synthesized according to the same method.

| a9 | 4-(2,2-difluoropropyl)pyrrolidin-2-one | LC-MS (MH$^+$): 164 |
|---|---|---|
| a10 | 4-[2-(benzyloxy)ethyl]pyrrolidin-2-one | LC-MS (MH$^+$): 220 |

(4S)-4-(3,3,3-trifluoropropyl)pyrrolidin-2-one a8S is obtained by separation by chiral chromatography of 4-(3,3,3-trifluoropropyl)pyrrolidin-2-one a8 (phase: Chiralpak AD-H; 30° C.; column: 250*4.6 mm; eluent: MeOH/EtOH/iso-hexane/diethylamine 8:2:90:0.1; 1 ml/min.).

LC-MS (MH$^+$): 182.

1.1.4 Synthesis of 4-(2,2-difluoroethyl)pyrrolidin-2-one a11

A solution of 4-(2,2-difluoroethenyl)pyrrolidin-2-one a1 (2.8 g, 18.77 mmol, 1 eq) and palladium on charcoal (10% Wt, 300 mg) in methanol (500 ml) is stirred overnight under an hydrogen atmosphere (40 psi) at room temperature. The reaction mixtured is filtered over celite and the solvent is removed under reduced pressure to afford 4-(2,2-difluoroethyl)pyrrolidin-2-one a11 which can be used in the next step without any further purification.

Yield: 100%.

LC-MS (MH$^+$): 150.

1.2 Synthesis of 4-substituted 1-(hydroxymethyl) pyrrolidin-2-ones and 4-substituted 1-(chloromethyl) pyrrolidin-2-ones These intermediates may be prepared according to the methods described in PCT patent applications WO2006128692, WO2006128693 and WO 2005054188.

| a12 | 4-(2-chloro-2,2-difluoroethyl)-1-(hydroxymethyl)pyrrolidin-2-one | LC-MS (MH$^+$): 214/216 |
|---|---|---|
| a12R | (4R)-4-(2-chloro-2,2-difluoroethyl)-1-(hydroxymethyl)pyrrolidin-2-one | LC-MS (MH$^+$): 214/216 |

-continued

| | | |
|---|---|---|
| a13 | 1-(hydroxymethyl)-4-(2,2,2-trifluoroethyl)pyrrolidin-2-one | LC-MS (MH+): 198 |
| a13R | (4R)-1-(hydroxymethyl)-4-(2,2,2-trifluoroethyl)pyrrolidin-2-one | LC-MS (MH+): 198 |
| a14 | 1-(hydroxymethyl)-4-(3,3,3-trifluoropropyl)pyrrolidin-2-one | LC-MS (MH+): 212 |
| a14S | (4S)-1-(hydroxymethyl)-4-(3,3,3-trifluoropropyl)pyrrolidin-2-one | LC-MS (MH+): 212 |
| a15 | 4-(2,2-difluoropropyl)-1-(hydroxymethyl)pyrrolidin-2-one | LC-MS (MH+): 194 |
| a16 | 4-[2-(benzyloxy)ethyl]-1-(hydroxymethyl)pyrrolidin-2-one | LC-MS (MH+): 236 |
| a17 | 4-(2,2-difluoroethyl)-1-(hydroxymethyl)pyrrolidin-2-one | LC-MS (MH+): 180 |
| a18 | 4-(2-chloro-2,2-difluoroethyl)-1-(chloromethyl)pyrrolidin-2-one | Not detectable in MS |
| a18R | (4R)-4-(2-chloro-2,2-difluoroethyl)-1-(chloromethyl)pyrrolidin-2-one | Not detectable in MS |
| a19 | 1-(chloromethyl)-4-(2,2,2-trifluoroethyl)pyrrolidin-2-one | Not detectable in MS |
| a19R | (4R)-1-(chloromethyl)-4-(2,2,2-trifluoroethyl)pyrrolidin-2-one | Not detectable in MS |
| a20 | 1-(chloromethyl)-4-(3,3,3-trifluoropropyl)pyrrolidin-2-one | Not detectable in MS |
| a20S | (4S)-1-(chloromethyl)-4-(3,3,3-trifluoropropyl)pyrrolidin-2-one | Not detectable in MS |
| a21 | 1-(chloromethyl)-4-(2,2-difluoropropyl)pyrrolidin-2-one | Not detectable in MS |
| a22 | 4-[2-(benzyloxy)ethyl]-1-(chloromethyl)pyrrolidin-2-one | Not detectable in MS |
| a23 | 1-(chloromethyl)-4-(2,2-difluoroethyl)pyrrolidin-2-one | Not detectable in MS |

Example 2

Synthesis of 4-(2-chloro-2,2-difluoroethyl)-1-{[2-(methoxymethyl)-6-(trifluoro-methyl)imidazo[2,1-b][1,3,4]thiadiazol-5-yl]methyl}pyrrolidin-2-one 4 and enantiomers

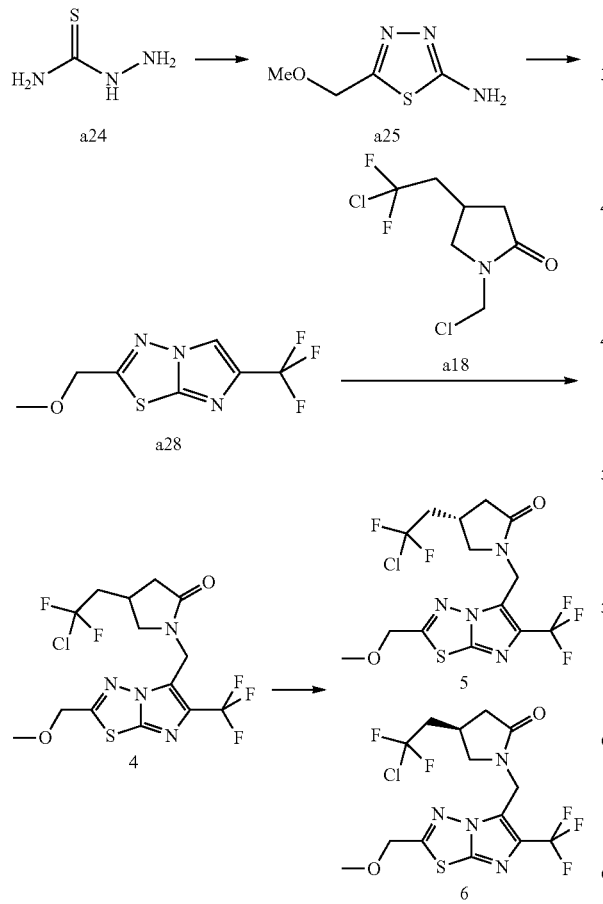

2.1 Synthesis of 5-(methoxymethyl)-1,3,4-thiadiazol-2-amine a25

To a suspension of thiosemicarbazide a24 (40 g, 0.44 mol, 1 eq) in dioxane (400 ml) at room temperature is added methoxyacetic acid (39.56 g, 0.44 mol, 1 eq) in one portion, and the reaction mixture is heated at 80° C. then phosphorous oxychloride (67.54 g, 0.44 mol, 1 eq) is carefully added over 1.5 hours. After reaction completion (4 hours), water is added and the solution is neutralised to pH=6-7 with sodium hydroxyde pellets. After extraction EtOAc/iPrOH (9/1) and evaporation under vacuum, the residue is recrystallized from MeTHF/iPrOH to afford 51 g of pure 5-(methoxymethyl)-1,3,4-thiadiazol-2-amine a25.

Yield: 81%.

LC-MS (MH+): 146.

5-[(benzyloxy)methyl]-1,3,4-thiadiazol-2-amine a26 (LC-MS (MH+): 222) and 5-(2-methoxyethyl)-1,3,4-thiadiazol-2-amine a40 (LC-MS (MH+): 160) may be obtained according to the same method.

LC-MS (MH+): 222.

Alternative method for the synthesis of 5-[(2,2,2-trifluoroethoxy)methyl]-1,3,4-thiadiazol-2-amine a27: a TFA (25 ml) solution of thiosemicarbazide a24 (4.9 g, 35 mmol, 1 eq) and (2,2,2-trifluoroethoxy)acetonitrile (3.2 g, 35 mmol, 1 eq) in TFA (25 ml) is heated at 60° C. for one hour. After cooling, the trifluoroacetic acid is removed under vacuum and the crude product is poured on iced sodium hydroxide solution (30 wt %, 50 ml) where the expected product crashed out. Filtration and subsequent drying of the crystalline product under vacuum afford 4.8 g of pure 5-[(2,2,2-trifluoroethoxy)methyl]-1,3,4-thiadiazol-2-amine a27 as a white solid (4.8 g, 64%).

Yield: 64%.

LC-MS (MH+): 214.

2.2 Synthesis of 2-(methoxymethyl)-6-(trifluoromethyl)imidazo[2,1-b][1,3,4]thiadiazole a28

Bromotrifluoroacetone (478 g, 1.05 eq) is added on a suspension of 5-(methoxymethyl)-1,3,4-thiadiazol-2-amine a25

(346 g, 1 eq) in 1,2-dimethoxyethane (6 l) at 20° C. The reaction mixture is heated to 80° C. until maximum conversion (<24 h). Water (4 l) is added to the reaction mixture at 32° C. and the expected compound crystallized out of the reaction mixture. The crystalline suspension is cooled to 10° C. to complete the crystallization process, filtered and the crystalline precipitate is washed with water (1.5 l) to afford 266 g of pure 2-(methoxymethyl)-6-(trifluoromethyl)imidazo[2,1-b][1,3,4]thiadiazole a28.

Yield: 47%.
LC-MS (MH⁺): 238.

The following compounds may be synthesized according to the same method.

| a29 | 2-[(benzyloxy)methyl]-6-(trifluoromethyl)imidazo[2,1-b][1,3,4]thiadiazole | LC-MS (MH⁺): 313 |
| a30 | 6-(difluoromethyl)-2-(methoxymethyl)imidazo[2,1-b][1,3,4]thiadiazole | LC-MS (MH⁺): 220 |
| a41 | 2-(2-methoxyethyl)-6-(trifluoromethyl)imidazo[2,1-b][1,3,4]thiadiazole | LC-MS (MH⁺): 252 |

2.3 Synthesis of 4-(2-chloro-2,2-difluoroethyl)-1-{[2-(methoxymethyl)-6-(trifluoro-methyl)imidazo[2,1-b][1,3,4]thiadiazol-5-yl]methyl}pyrrolidin-2-one 4 and enantiomers 5 and 6

To a hot solution (80° C.) of ZnCl₂ (0.23 g, 1.69 mmol, 10 mol %) and 2-(methoxymethyl)-6-(trifluoromethyl)imidazo[2,1-b][1,3,4]thiadiazole a28 (4 g, 16.96 mmol) in dioxane (200 ml) is added a solution of 4-(2-chloro-2,2-difluoroethyl)-1-(chloromethyl)pyrrolidin-2-one a18 in dioxane (5 ml). The reaction mixture is heated at 85° C. for 5 days, then a further 2 g of pyrrolidinone a18 is added in one portion and the reaction mixture is kept under agitation at 90° C. for 1 day. A further addition of pyrrolidinone a18 (2 g) in order to insure complete conversion of compound a28 and further heating of the reaction mixture at reflux for 3 days increased significatively the conversion of imidazo[2,1-b][1,3,4]thiadiazole a28. After cooling and hydrolysis (250 ml of water), the crude mixture is extracted by CH₂Cl₂ (2×250 ml). The cumulated organic layers are dried over MgSO₄, filtered and condensed under reduced pressure. The residue is purified over silicagel (eluent: CH₂Cl₂/MeOH/NH₄OH 99/1/0.1) to afford 4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one 4.

Yield: 74%.
LC-MS (MH⁺): 433/435.

The enantiomers are separated by chiral chromatography (phase:Chiralpak AS-V; 30° C.; column: 50*500 mm; eluent: ethanol/n-heptane 30:70).

Pure (4S)-4-(2-chloro-2,2-difluoroethyl)-1-{[2-(methoxymethyl)-6-(trifluoromethyl) imidazo[2,1-b][1,3,4]thiadiazol-5-yl]methyl}pyrrolidin-2-one 5 (2.10 g) is obtained after recrystallization in CH₂Cl₂/hexane.

Yield: 28.6%.
LC-MS (MH⁺): 433/435.

Pure (4R)-4-(2-chloro-2,2-difluoroethyl)-1-{[2-(methoxymethyl)-6-(trifluoromethyl) imidazo[2,1-b][1,3,4]thiadiazol-5-yl]methyl}pyrrolidin-2-one 6 (2.15 g) is obtained after recrystallization in CH₂Cl₂/hexane.

Yield: 29.3%.
LC-MS (MH⁺): 433/435.

Compounds 1, 2, 3, 10, 11, 12, 14, 15, 16, 18, 19, 20, 21, 22, 23, 33, 34 and 35 may be synthesized according to the same method.

Example 3

Synthesis of (+)-1-{[6-chloro-2-(methoxymethyl)imidazo[2,1-b][1,3,4]thiadiazol-5-yl]methyl}-4-(3,3,3-trifluoropropyl)pyrrolidin-2-one 27

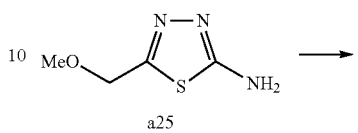

a25

-continued

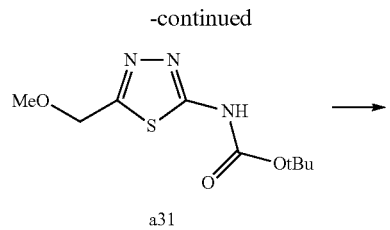

a31

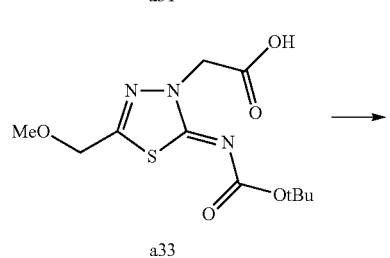

a33

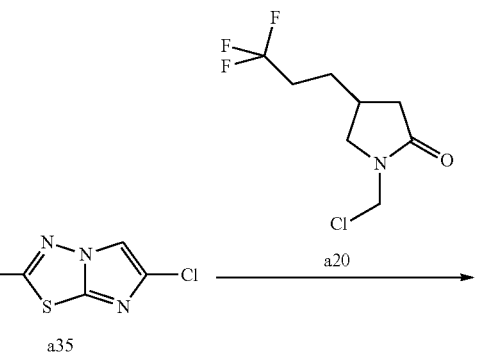

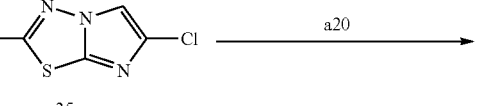

a35

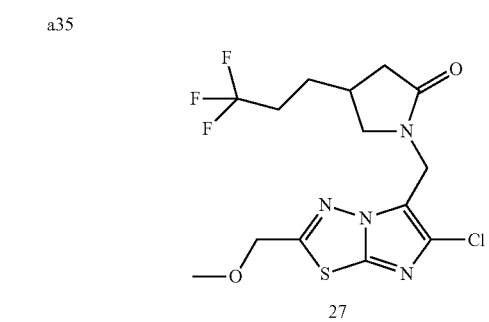

27

3.1 Synthesis of tert-butyl [5-(methoxymethyl)-1,3,4-thiadiazol-2-yl]carbamate a31

To a suspension of 5-(methoxymethyl)-1,3,4-thiadiazol-2-amine a25 (100 g, 0.69 mol, 1 eq) in dichloromethane (1 l) at room temperature is added, successively and each in one portion, di-tert-butyl dicarbonate (132 g, 0.76 mol, 1.1 eq,) and N,N-dimethylamino-pyridine (8.35 g, 0.069 mol, 0.1 eq). After overnight stirring at room temperature, the reaction mixture is washed with 1N HCl (pH 5) to remove N,N-dimethylaminopyridine. The solvent is then removed under reduced pressure and the residue is recrystallized from di-isopropyl ether to afford 148.9 g of pure tert-butyl [5-(methoxymethyl)-1,3,4-thiadiazol-2-yl]carbamate a31.

Yield: 88.1%.
LC-MS (MH$^+$): 246.

Tert-butyl {5-[(2,2,2-trifluoroethoxy)methyl]-1,3,4-thiadiazol-2-yl}carbamate a32 may be synthesized according to the same method.
LC-MS (MH$^+$): 314.

3.2 Synthesis of {2-[(tert-butoxycarbonyl)imino]-5-(methoxymethyl)-1,3,4-thiadiazol-3(2H)-yl}acetic acid a33

Iodoacetic acid (409.3 g, 2.2 mol, 1.5 eq) is added in one portion to a solution of tert-butyl [5-(methoxymethyl)-1,3,4-thiadiazol-2-yl]carbamate a31 (360 g, 1.468 mol, 1 eq) in tetrahydrofurane (3 l) at room temperature. Sodium hydride (52.83 g, 2.2 mol, 1.5 eq) is then added portionwise, in 30 minutes, at room temperature. The reaction mixture is heated at 60° C. for the night, and the solvent is evaporated under reduced pressure. Water is added to the residue, the solution is acidified to pH=2 with aqueous 6N HCl, then extracted with $CH_2Cl_2$. The organic layer is washed with 10% aqueous $Na_2S_2O_3$ (to remove the coloration of iodine) and evaporated to dryness to furnish 455.7 g of {2-[(tert-butoxycarbonyl)imino]-5-(methoxymethyl)-1,3,4-thiadiazol-3(2H)-yl}acetic acid a33 which is used directly in the next step without any further purification.

Yield: 89.8%.
LC-MS (MH$^+$): 304.
{2-[(tert-butoxycarbonyl)imino]-5-[(2,2,2-trifluoroethoxy)methyl]-1,3,4-thiadiazol-3(2H)-yl}acetic acid a34 may be synthesized according to the same method.
LC-MS (MH$^+$): 372.

3.3 Synthesis of 6-chloro-2-(methoxymethyl)imidazo[2,1-b][1,3,4]thiadiazole a35

To {2-[(tert-butoxycarbonyl)imino]-5-(methoxymethyl)-1,3,4-thiadiazol-3(2H)-yl}acetic acid a33 (418 g, 1.378 mol, 1 eq) in acetonitrile (2.5 l) at room temperature, are successively and slowly added triethyl amine (278.9 g, 2.756 mol, 2 eq), then phosphorous oxychloride (633.9 g, 4.134 mol, 3 eq). The reaction mixture is heated at 80° C. for one hour. After reaction completion, water (2.2 l) is slowly and carefully added at 50° C. The reaction mixture is extracted with dichloromethane (2×1.2 l), the combined organic layers are washed by a NaOH/NaCl aqueous solution (1.4 l of saturated NaCl solution+400 ml 2N NaOH), dried over $MgSO_4$, filtered and condensed under reduced pressure. The residue is recrystallized from acetonitrile/water (1/1) to afford 99.8 g of pure 6-chloro-2-(methoxymethyl)imidazo[2,1-b][1,3,4]thiadiazole a35.

Yield: 35.6%.
LC-MS (MH$^+$): 204/206.

6-chloro-2-[(2,2,2-trifluoroethoxy)methyl]imidazo[2,1-b][1,3,4]thiadiazole a36 may be synthesized according to the same method.
LC-MS (MH$^+$): 272/274.

3.4 Synthesis of (+)-1-{[6-chloro-2-(methoxymethyl)imidazo[2,1-b][1,3,4]thiadiazol-5-yl]methyl}-4-(3,3,3-trifluoropropyl)pyrrolidin-2-one 27

To a hot solution (80° C.) of $AlCl_3$ (0.842 g, 6.3 mmol, 1 eq) and 6-chloro-2-(methoxy-methyl)imidazo[2,1-b][1,3,4]thiadiazole a35 (0.643 g, 3.156 mmol, 1 eq) in dioxane (35 ml) is added a solution of 1-(chloromethyl)-4-(3,3,3-trifluoropropyl)pyrrolidin-2-one a20 (1.2 g) in dioxane (5 ml). The reaction mixture is heated at 85° C. for 3 days. After cooling and hydrolysis by a saturated solution of $NaHCO_3$ (40 ml), the crude reaction mixture is extracted by ethyl acetate (3×25 ml). The cumulated organic layers are dried over $MgSO_4$, filtered and condensed under reduced pressure. The residue is purified by chromatography over silicagel (eluent $CH_2Cl_2$/MeOH/$NH_4OH$ 99:1:0.1) and recrystallized from diisopropyl ether to afford pure (+)-1-{[6-chloro-2-(methoxymethyl)-imidazo[2,1-b][1,3,4]thiadiazol-5-yl]methyl}-4-(3,3,3-trifluoropropyl)pyrrolidin-2-one 27.

Yield: 56%.
LC-MS (MH$^+$): 397/399.

Compounds 24, 25 and 26 may be synthesized according to the same method. 4-[2-(benzyloxy)ethyl]-1-{[6-chloro-2-(methoxymethyl)imidazo[2,1-b][1,3,4]thiadiazol-5-yl]methyl}pyrrolidin-2-one a37 may also be synthesized according to the same method.
LC-MS (MH$^+$): 435/437.

Example 4

Synthesis of 1-{[6-chloro-2-(methoxymethyl)imidazo[2,1-b][1,3,4]thiadiazol-5-yl]methyl}-4-(2-fluoroethyl)pyrrolidin-2-one 28

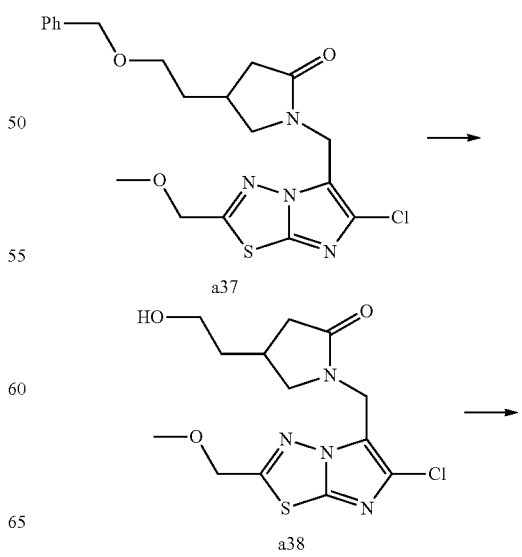

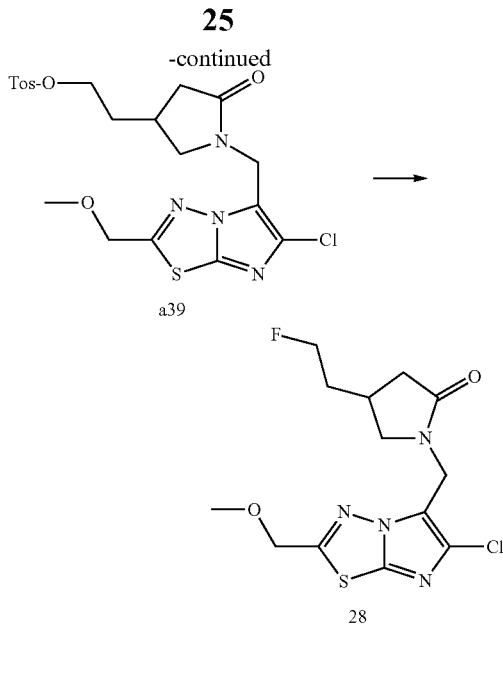

4.1 Synthesis of 2-(1-{[6-chloro-2-(methoxymethyl) imidazo[2,1-b][1,3,4]thiadiazol-5-yl]methyl}-5-oxopyrrolidin-3-yl)ethyl 4-methylbenzenesulfonate a39

4-[2-(benzyloxy)ethyl]-1-{[6-chloro-2-(methoxymethyl) imidazo[2,1-b][1,3,4]thiadiazol-5-yl]methyl}pyrrolidin-2-one a37 (300 mg, 0.69 mmol, 1 eq) is heated at 60° C. for 3 hours in trifluoroacetic acid (3 ml). The crude 1-{[6-chloro-2-(methoxymethyl)imidazo[2,1-b][1,3,4]thiadiazol-5-yl]methyl}-4-(2-hydroxyethyl)pyrrolidin-2-one a38 is obtained after cooling and evaporation of the volatiles under reduced pressure. Dichloromethane (10 ml) is added to the residue, the mixture is cooled to 0° C., then tosyl chloride (158 mg, 0.828 mmol, 1.2 eq), triethyl amine (0.48 ml, 3.45 mmol, 5 eq) and 4-dimethylamino-pyridine (8 mg, 10 mol %,) are added at 0° C. The reaction is kept for 1 h at 0° C., then warmed up to room temperature and stirring is pursued for 2 days. After hydrolysis ($H_2O$, 10 ml) and extraction with $CH_2Cl_2$ (4×10 ml), the cumulated organic layers are dried over $MgSO_4$, filtered and evaporated under reduced pressure. The residue is purified by flash chromatography over silicagel (eluent: $CH_2Cl_2$/MeOH 97:3) to afford 308 mg of 2-(1-{[6-chloro-2-(methoxymethyl)imidazo[2,1-b][1,3,4]thiadiazol-5-yl]methyl}-5-oxopyrrolidin-3-yl)ethyl 4-methylbenzenesulfonate a39.

Yield: 89%.
LC-MS ($MH^+$): 246.

4.2 Synthesis of 1-{[6-chloro-2-(methoxymethyl) imidazo[2,1-b][1,3,4]thiadiazol-5-yl]methyl}-4-(2-fluoroethyl)pyrrolidin-2-one 28

A 1M solution of tetrabutylammonium fluoride in THF solution (4 ml) is added to 2-(1-{[6-chloro-2-(methoxymethyl)imidazo[2,1-b][1,3,4]thiadiazol-5-yl]methyl}-5-oxopyrrolidin-3-yl)ethyl 4-methylbenzenesulfonate a39 (308 mg, 0.617 mmol, 1 eq). The resulting solution is irradiated in a microwave apparatus (Biotage) at 100° C. for 1 h. Water (10 ml) is added to the reaction mixture, and the crude compound is extracted by ethyl acetate (4×10 ml). The cumulated organic layer are washed successively by a saturated $NH_4Cl$ aqueous solution (2×10 ml), water (2×10 ml), dried over $MgSO_4$, filtered and condensed under reduced pressure. The residue is purified by flash chromatography over silicagel (eluent: $CH_2Cl_2$/MeOH 99:1) to afford 47 mg of pure 1-{[6-chloro-2-(methoxymethyl)-imidazo[2,1-b][1,3,4]thiadiazol-5-yl]methyl}-4-(2-fluoroethyl)pyrrolidin-2-one 28.

Yield: 22%.
LC-MS ($MH^+$): 347/349.

Example 5

Synthesis of 4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one 7

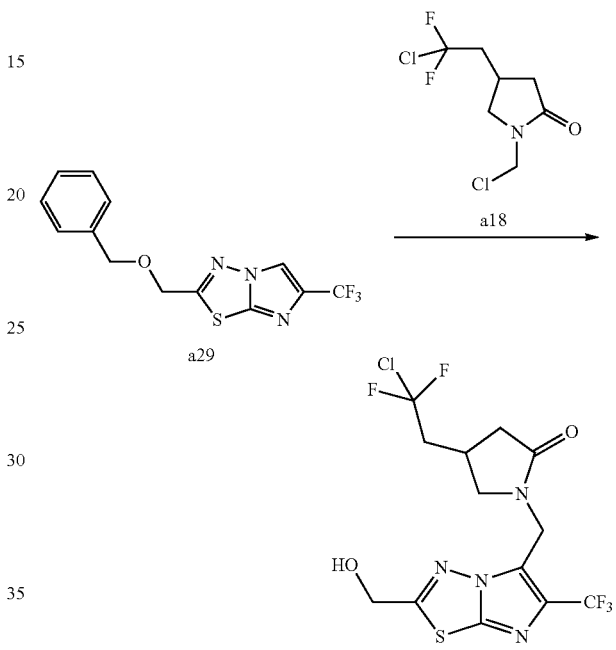

A solution of 4-(2-chloro-2,2-difluoroethyl)-1-(chloromethyl)pyrrolidin-2-one a18 in dioxane (5 ml) is added to a hot solution (90° C.) of dry $ZnCl_2$ (0.272 g, 2 mmol, 0.5 eq) and 2-[(benzyloxy)methyl]-6-(trifluoromethyl)imidazo[2,1-b][1,3,4]thiadiazole a29 (1.3 g, 4 mmol, 1 eq) in dioxane (5 ml). The reaction mixture is heated at 90° C. for 3 days and 1,4-dioxane is removed under reduced pressure. The crude reaction mixture is taken up in trifluoroacetic acid (20 ml) and heated at 60° C. for 2 hours. After cooling, the trifluoro-acetic acid is removed under reduced pressure. The residue is purified by chromatography on silicagel (MeOH/$CH_2Cl_2$) and pure 4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one 7 (573 mg) is obtained after re-crystallization from ethyl acetate.

Yield: 36%.
LC-MS ($MH^+$): 419/421.

Compounds 13, 29 and 17 may be synthesized according to the same method.

The enantiomers of compound 7 are separated by chiral chromatography (phase: Chiralpak AS-V; 30° C.; column: 50*500 mm; eluent: iPrOH/n-heptane 50:50) to afford (4R)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one 8 and (4S)-4-(2-chloro-2,2-difluoroethyl)-1-{[2-(hydroxymethyl)-6-(trifluoromethyl)imidazo[2,1-b][1,3,4]thiadiazol-5-yl]methyl}-pyrrolidin-2-one 9.

Example 6

Synthesis of (4R)-4-(2-chloro-2,2-difluoroethyl)-1-{[2-{[(²H₃)methyloxy]methyl}-6-(trifluoromethyl)imidazo[2,1-b][1,3,4]thiadiazol-5-yl]methyl}pyrrolidin-2-one 30

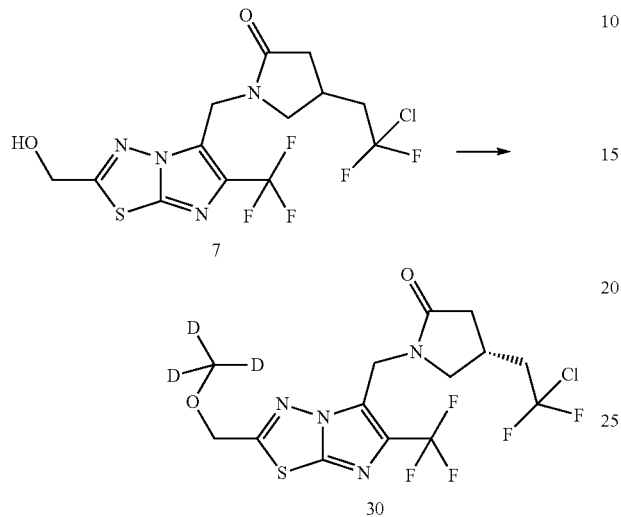

A solution of 4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one 7 (0.2 g, 0.48 mmol, 1 eq) and cesium hydroxide (0.16 g, 0.96 mmol, 2 eq) in tetrahydrofuran (10 ml) is treated with perdeuterated methyl iodide (0.277 g, 1.91 mmol, 4 eq). The mixture is stirred at 22° C. for 24 h. It is then diluted with ethyl acetate and washed with water (2×10 ml) and with brine. The organic layer is dried over magnesium sulphate and concentrated under reduced pressure to afford an orange oil. It is purified by reverse phase HPLC(X-bridge C18, eluent: MeCN/H₂O/NH₃) to afford 100 mg of a pale yellow oil. It is triturated in diisopropyl ether and filtered. The resulting solid is dried under reduced pressure at 40° C. to afford 50 mg of (4R)-4-(2-chloro-2,2-difluoroethyl)-1-{[2-{[(²H₃)methyloxy]methyl}-6-(trifluoromethyl)imidazo[2,1-b][1,3,4]thiadiazol-5-yl]methyl}pyrrolidin-2-one 30 as a white solid.
Yield: 42%.
LC-MS (MH⁺): 436/438.

Example 7

Synthesis of (4R)-4-(2-chloro-2,2-difluoroethyl)-1-({2-[methoxy(²H₂)methyl]-6-(trifluoromethyl)imidazo[2,1-b][1,3,4]thiadiazol-5-yl}methyl)pyrrolidin-2-one 31

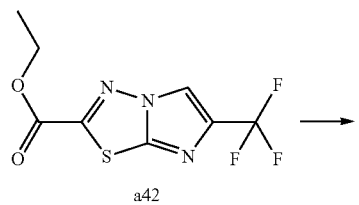

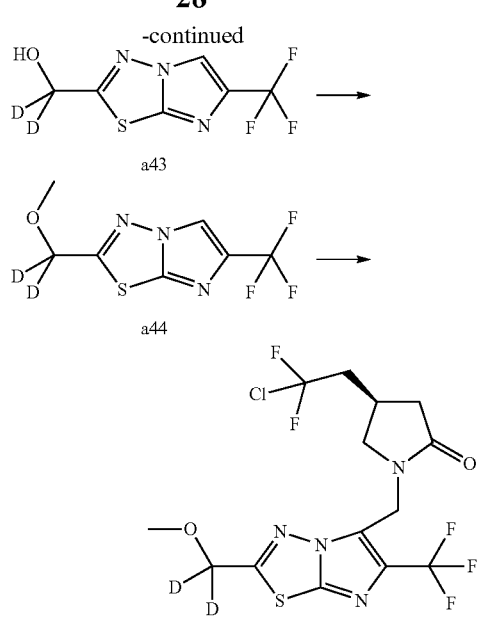

7.1 Synthesis of ethyl 6-(trifluoromethyl)imidazo[2,1-b][1,3,4]thiadiazole-2-carboxylate a42

Ethyl 6-(trifluoromethyl)imidazo[2,1-b][1,3,4]thiadiazole-2-carboxylate a42 is prepared as described in example 2 from commercially available ethyl 5-amino-1,3,4-thiadiazole-2-carboxylate.
Yield: 24%.
LC-MS (MH⁺): 266.

7.2 Synthesis of [6-(trifluoromethyl)imidazo[2,1-b][1,3,4]thiadiazol-2-yl](²H₂)methanol a43

A solution of ethyl 6-(trifluoromethyl)imidazo[2,1-b][1,3,4]thiadiazole-2-carboxylate a42 (1 g, 3.77 mmol, 1 eq) in ethanol (20 ml) is treated with sodium borodeuteride (0.316 g, 7.54 mmol, 2 eq). The mixture is stirred under stirring at 22° C. for 24 h. The mixture is then poured in water and extracted with ethyl acetate. The organic layer is dried over magnesium sulphate and concentrated under reduced pressure to afford 554 mg of [6-(trifluoromethyl)imidazo[2,1-b][1,3,4]thiadiazol-2-yl](²H₂)methanol a43 as an orange oil. This oil is used in the next step without any further purification.
Yield: 65%.
LC-MS (MH⁺): 226.

7.3 Synthesis of 2-[methoxy(²H₂)methyl]-6-(trifluoromethyl)imidazo[2,1-b][1,3,4]thiadiazole a44

A solution of [6-(trifluoromethyl)imidazo[2,1-b][1,3,4]thiadiazol-2-yl](²H₂)methanol a43 (554 mg, 2.46 mmol, 1 eq) and cesium hydroxide (0.826 g, 4.92 mmol, 2 eq) in tetrahydrofuran (50 ml) is treated with methyl iodide (612 μl, 9.84 mmol, 4 eq). The mixture is stirred 24 h at 22° C. It is then diluted with ethyl acetate and washed with water (3×50 ml). The organic layer is dried over magnesium sulphate and concentrated under reduced pressure to afford 560 mg of an orange oil. It is purified by chromatography over silicagel (eluent: CH₂Cl₂/heptane 50:50, 23 ml/min, room temperature) to afford 307 mg of 2-[methoxy($^2H_2$)methyl]-6-(trifluoromethyl)imidazo[2,1-b][1,3,4]thiadiazole a44.

Yield: 59%.

LC-MS (MH$^+$): 240.

7.4 Synthesis of (4R)-4-(2-chloro-2,2-difluoroethyl)-1-({2-[methoxy($^2H_2$)methyl]-6-(trifluoromethyl)imidazo[2,1-b][1,3,4]thiadiazol-5-yl}methyl)pyrrolidin-2-one 31

A solution of (4R)-4-(2-chloro-2,2-difluoroethyl)-1-(hydroxymethyl)pyrrolidin-2-one a12R (0.281 g, 1.32 mmol, 1.5 eq) in dichloromethane (25 ml) is treated with thionyl chloride (382 μl, 5.27 mmol, 6 eq). The mixture is stirred for 1 h at 22° C. and concentrated in vacuo to obtain (4R)-4-(2-chloro-2,2-difluoroethyl)-1-(chloromethyl)pyrrolidin-2-one a18R. The resulting liquid is then added to a solution of anhydrous zinc chloride (0.239 g, 1.76 mmol, 2 eq) and 2-[methoxy($^2H_2$)methyl]-6-(trifluoromethyl)imidazo[2,1-b][1,3,4]thiadiazole a44 (0.210 g, 0.88 mmol, 1 eq) in dioxane. The mixture is stirred at 80° C. for 4 days. Some more (4R)-4-(2-chloro-2,2-difluoroethyl)-1-(hydroxymethyl)pyrrolidin-2-one a12R (1.5 eq) are then added and the mixture is stirred for another 24 h. (4R)-4-(2-chloro-2,2-difluoroethyl)-1-(hydroxymethyl)pyrrolidin-2-one a12R (2 eq) is added again and the mixture stirred for another 3 days. The mixture is then diluted with dichloromethane and washed with water (2×25 ml). The organic layer is dried over magnesium sulphate and concentrated under reduced pressure to afford 1.28 g of a brown oil. The mixture is purified by reverse phase HPLC (X-bridge C18, eluent: MeCN/H$_2$O/NH$_3$) to afford (4R)-4-(2-chloro-2,2-difluoroethyl)-1-({2-[methoxy($^2H_2$)methyl]-6-(trifluoromethyl)imidazo[2,1-b][1,3,4]thiadiazol-5-yl}methyl)pyrrolidin-2-one 31 as a yellow oil.

Yield: 36%.

LC-MS (MH$^+$): 435/437.

Example 8

Synthesis of (4R)-4-(2-chloro-2,2-difluoroethyl)-1-{[2-(methoxymethyl)-6-trifluoromethyl)imidazo[2,1-b][1,3,4]thiadiazol-5-yl]($^2H_2$)methyl}pyrrolidin-2-one 32

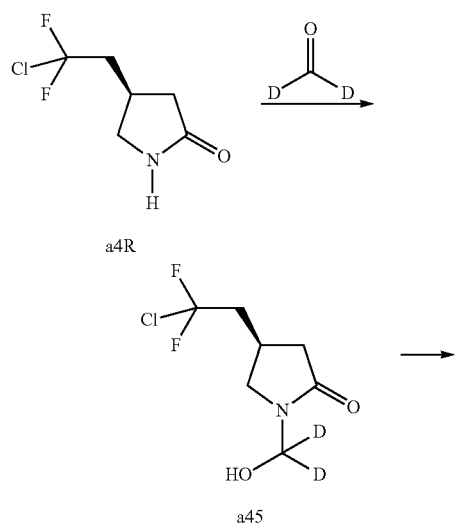

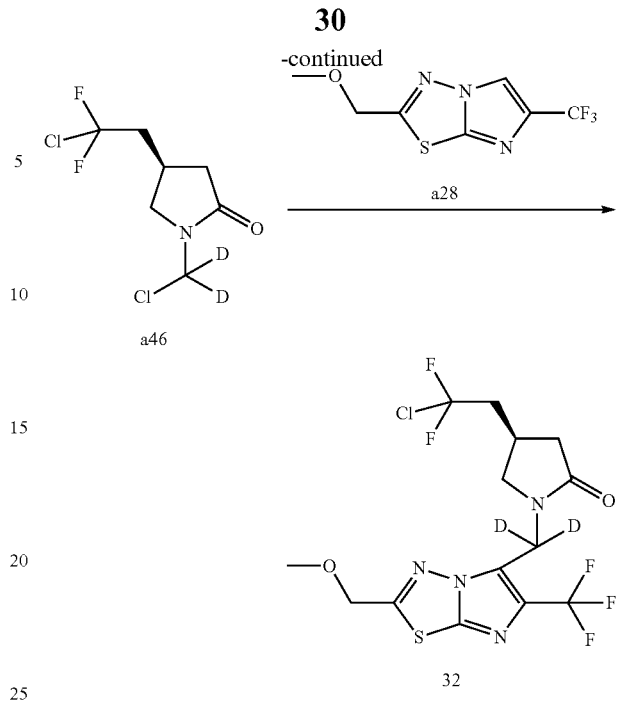

8.1 Synthesis of (4R)-4-(2-chloro-2,2-difluoroethyl)-1-[hydroxy($^2H_2$)methyl]pyrrolidin-2-one a45

(4R)-4-(2-chloro-2,2-difluoroethyl)-1-(chloromethyl)pyrrolidin-2-one a4R (1.67 g) is suspended in water and (5.1 ml) cooled to 0° C. After addition of a catalytic amount of potassium hydroxide (0.03 g, 0.05 eq mol), a 10% w/w aqueous solution of deuterated formaldehyde is added (3.4 g, 1.2 eq mol) maintaining the temperature below 5° C. After reaction completion (checked by HPLC), the product is quenched with sodium bisulfite, extracted with methylene chloride and evaporated to dryness to afford 1.89 g of (4R)-4-(2-chloro-2,2-difluoroethyl)-1-[hydroxy($^2H_2$)methyl]pyrrolidin-2-one a45.

Yield: 95%.

LC-MS (MH$^+$): 216/218.

8.2 Synthesis of (4R)-4-(2-chloro-2,2-difluoroethyl)-1-[chloro($^2H_2$)methyl]pyrrolidin-2-one a46

(4R)-4-(2-chloro-2,2-difluoroethyl)-1-[hydroxy($^2H_2$)methyl]pyrrolidin-2-one a45 (0.80 g) is dissolved in methylene chloride (5 ml) and cooled to 0° C. Thionyl chloride (0.44 g, 1.05 eq mol) diluted with methylene chloride (1 ml) is then added dropwise. After reaction completion, the mixture is stripped to dryness to afford (4R)-4-(2-chloro-2,2-difluoroethyl)-1-[chloro($^2H_2$)methyl]pyrrolidin-2-one a46 and is used as such for the next step.

8.3 Synthesis of (4R)-4-(2-chloro-2,2-difluoroethyl)-1-{[2-(methoxymethyl)-6-(trifluoromethyl)imidazo[2,1-b][1,3,4]thiadiazol-5-yl]-($^2H_2$)methyl}pyrrolidin-2-one 32

(4R)-4-(2-chloro-2,2-difluoroethyl)-1-[chloro($^2H_2$)methyl]pyrrolidin-2-one a46 is redissolved in dry dioxane (3.4 ml) and is added at 90° C. to a mixture of 2-(methoxymethyl)-6-(trifluoromethyl)imidazo[2,1-b][1,3,4]thiadiazole a28 (0.85 g, 1.0 eq mol) and zinc chloride (0.27 g, 0.55 eq mol) in dioxane (5 ml). The reaction mixture is stirred for 5 days at this temperature. After reaction completion and extractive work-up, the product is purified by preparative reverse phase chromatography (eluent: CH₃CN/H₂O/NH₄OH 30/70/0.1) followed by a chromatography over normal phase (eluent: CH₂Cl₂/EtOH/NH₄OH 99.5/0.5/0.05) to afford 0.46 g of (4R)-4-(2-chloro-2,2-difluoroethyl)-1-{[2-(methoxymethyl)-6-(trifluoromethyl)imidazo[2,1-b][1,3,4]thiadiazol-5-yl](²H₂)methyl}pyrrolidin-2-one 32.

Yield: 30%.

LC-MS (MH⁺): 435/437.

Table I indicates the IUPAC name of the compound, the ion peak observed in mass spectroscopy, the ¹H NMR description, the melting point or onset on DSC, and the alpha$_D$.

TABLE I

Physical Characterization of Example Compounds.

| n° | IUPAC NAME | MH⁺ | ¹H NMR δ (CDCl₃ otherwise specified) | MP° C. (DSC) | alpha$_D$ |
|---|---|---|---|---|---|
| 1 | 4-(2,2-difluoropropyl)-1-{[2-(methoxymethyl)-6-(trifluoromethyl)imidazo[2,1-b][1,3,4]thiadiazol-5-yl]methyl}pyrrolidin-2-one | 413 | 4.90 (m, 2 H), 4.75 (s, 2 H), 3.52 (m, 3 H), 3.42 (m, 1 H), 2.99 (m, 1 H), 2.63 (m, 2 H), 2.18 (m, 1 H), 1.97 (m, 2 H), 1.59 (s, 3H) | | |
| 2 | (+)-4-(2,2-difluoropropyl)-1-{[2-(methoxymethyl)-6-(trifluoromethyl)imidazo[2,1-b][1,3,4]thiadiazol-5-yl]methyl}pyrrolidin-2-one | 413 | 4.90 (m, 2 H), 4.75 (s, 2 H), 3.52 (m, 3 H), 3.42 (m, 1 H), 2.99 (m, 1 H), 2.63 (m, 2 H), 2.18 (m, 1 H), 1.97 (m, 2 H), 1.59 (s, 3H) | 70 | +0.056 |
| 3 | (−)-4-(2,2-difluoropropyl)-1-{[2-(methoxymethyl)-6-(trifluoromethyl)imidazo[2,1-b][1,3,4]thiadiazol-5-yl]methyl}pyrrolidin-2-one | 413 | 4.90 (m, 2 H), 4.75 (s, 2 H), 3.52 (m, 3 H), 3.42 (m, 1 H), 2.99 (m, 1 H), 2.63 (m, 2 H), 2.18 (m, 1 H), 1.97 (m, 2 H), 1.59 (s, 3H) | 67 | −0.046 |
| 4 | 4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one trifluoroacetate | 433/435 | (DMSO) 4.90 (dd, J = 30, 9 Hz, 2 H), 4.75 (s, 2 H), 3.52 (s, 3 H), 3.48 (m, 1 H), 3.04 (m, 1 H), 2.71 (m, 2 H), 2.46 (m, 2 H), 2.22 (m, 1 H) | | |
| 5 | (4S)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one | 433/435 | 4.90 (dd, J = 30, 9 Hz, 2 H), 4.75 (s, 2 H), 3.52 (s, 3 H), 3.48 (m, 1 H), 3.04 (m, 1 H), 2.71 (m, 2 H), 2.46 (m, 2 H), 2.22 (m, 1 H) | | −0.045 |
| 6 | (4R)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one | 433/435 | 4.90 (dd, J = 30, 9 Hz, 2 H), 4.75 (s, 2 H), 3.52 (s, 3 H), 3.48 (m, 1 H), 3.04 (m, 1 H), 2.71 (m, 2 H), 2.46 (m, 2 H), 2.22 (m, 1 H) | 83 | +0.050 |
| 7 | 4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one | 419/421 | (DMSO) 6.52 (s, 1 H), 4.77 (m, 4 H), 3.42 (t, J = 8.0 Hz, 1 H), 3.05 (m, 1 H), 2.63 (m, 3 H), 2.43 (dd, J = 16.6, 8.3 Hz, 1 H), 2.17 (dd, J = 16.6, 8.8 Hz, 1 H) | | |
| 8 | (4R)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one | 419/420 | (DMSO) 6.52 (s, 1 H), 4.77 (m, 4 H), 3.42 (t, J = 8.0 Hz, 1 H), 3.05 (m, 1 H), 2.63 (m, 3 H), 2.43 (dd, J = 16.6, 8.3 Hz, 1 H), 2.17 (dd, J = 16.6, 8.8 Hz, 1 H) | 154 | +0.027 |
| 9 | (4S)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one | 419/421 | (DMSO) 6.52 (s, 1 H), 4.77 (m, 4 H), 3.42 (t, J = 8.0 Hz, 1 H), 3.05 (m, 1 H), 2.63 (m, 3 H), 2.43 (dd, J = 16.6, 8.3 Hz, 1 H), 2.17 (dd, J = 16.6, 8.8 Hz, 1 H) | | |
| 10 | 1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one | 417 | (DMSO) 4.90 (m, 2 H), 4.74 (m, 2 H), 3.52 (s, 3 H), 3.47 (t, J = 6 Hz, 1 H), 3.03 (m, 1 H), 2.65 (t, J = 6 Hz, 2 H), 2.23 (m, 3 H) | | |
| 11 | (4R)-1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one | 417 | (DMSO) 4.90 (m, 2 H), 4.74 (m, 2 H), 3.52 (s, 3 H), 3.47 (t, J = 6 Hz, 1 H), 3.03 (m, 1 H), 2.65 (t, J = 6 Hz, 2 H), 2.23 (m, 3 H) | 72 | +0.045 |
| 12 | (4S)-1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one | 417 | (DMSO) 4.90 (m, 2 H), 4.74 (m, 2 H), 3.52 (s, 3 H), 3.47 (t, J = 6 Hz, 1 H), 3.03 (m, 1 H), 2.65 (t, J = 6 Hz, 2 H), 2.23 (m, 3 H) | 73 | −0.050 |

TABLE I-continued

Physical Characterization of Example Compounds.

| n° | IUPAC NAME | MH+ | ¹H NMR δ (CDCl₃ otherwise specified) | MP° C. (DSC) | alpha_D |
|---|---|---|---|---|---|
| 13 | 1-{[2-(hydroxymethyl)-6-(trifluoromethyl)imidazo[2,1-b][1,3,4]thiadiazol-5-yl]methyl}-4-(2,2,2-trifluoroethyl)pyrrolidin-2-one | 403 | (DMSO) 6.52 (s, 1 H), 4.86 (s, 2 H), 4.75 (m, 2 H), 3.40 (t, J = 8.8 Hz, 1 H), 3.03 (m, 1 H), 2.56 (m, 1 H), 2.42 (m, 3 H), 2.15 (dd, J = 16.3, 8.5 Hz, 1 H) | | |
| 14 | 1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one | 431 | (DMSO) 4.90 (s, 2 H), 4.75 (s, 2 H), 3.52 (s, 3 H), 3.41 (m, 1 H), 2.89 (dd, J = 9.7, 6.6 Hz, 1 H), 2.60 (dd, J = 16.7, 8.8 Hz, 1 H), 2.37 (m, 1 H), 2.06 (m, 3 H), 1.66 (m, 2 H) | | |
| 15 | (4S)-1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one | 431 | (DMSO) 4.90 (s, 2 H), 4.75 (s, 2 H), 3.52 (s, 3 H), 3.41 (m, 1 H), 2.89 (dd, J = 9.7, 6.6 Hz, 1 H), 2.60 (dd, J = 16.7, 8.8 Hz, 1 H), 2.37 (m, 1 H), 2.06 (m, 3 H), 1.66 (m, 2 H) | 63 | +0.044 |
| 16 | (4R)-1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one | 431 | (DMSO) 4.90 (s, 2 H), 4.75 (s, 2 H), 3.52 (s, 3 H), 3.41 (m, 1 H), 2.89 (dd, J = 9.7, 6.6 Hz, 1 H), 2.60 (dd, J = 16.7, 8.8 Hz, 1 H), 2.37 (m, 1 H), 2.06 (m, 3 H), 1.66 (m, 2 H) | (63.36) | −0.026 |
| 17 | (4S)-1-{[2-(hydroxymethyl)-6-(trifluoromethyl)imidazo[2,1-b][1,3,4]thiadiazol-5-yl]methyl}-4-(3,3,3-trifluoropropyl)pyrrolidin-2-one | 417 | (DMSO) 6.52 (s, 1 H), 4.84 (s, 2 H), 4.76 (m, 2 H), 3.35 (m, 1 H), 2.89 (dd, J = 9.3, 6.5 Hz, 1 H), 2.41 (m, 1 H), 2.24 (m, 3 H), 2.03 (dd, J = 16.3, 7.3 Hz, 1 H), 1.53 (m, 2 H) | | +0.029 |
| 18 | 4-(2,2-difluoroethyl)-1-{[2-(methoxymethyl)-6-(trifluoromethyl)imidazo[2,1-b][1,3,4]thiadiazol-5-yl]methyl}pyrrolidin-2-one | 399 | 5.83 (tt, J = 55.9, 4.0 Hz, 1 H), 4.90 (m, 2 H), 4.75 (s, 2 H), 3.52 (s, 3 H), 3.45 (m, 1 H), 2.99 (m, 1 H), 2.62 (m, 2 H), 2.18 (m, 1 H), 1.97 (m, 2 H) | | |
| 19 | (+)-4-(2,2-difluoroethyl)-1-{[2-(methoxymethyl)-6-(trifluoromethyl)imidazo[2,1-b][1,3,4]thiadiazol-5-yl]methyl}pyrrolidin-2-one | 399 | 5.83 (tt, J = 55.9, 4.0 Hz, 1 H), 4.90 (m, 2 H), 4.75 (s, 2 H), 3.52 (s, 3 H), 3.45 (m, 1 H), 2.99 (m, 1 H), 2.62 (m, 2 H), 2.18 (m, 1 H), 1.97 (m, 2 H) | | +0.041 |
| 20 | (−)-4-(2,2-difluoroethyl)-1-{[2-(methoxymethyl)-6-(trifluoromethyl)imidazo[2,1-b][1,3,4]thiadiazol-5-yl]methyl}pyrrolidin-2-one | 399 | 5.83 (tt, J = 55.9, 4.0 Hz, 1 H), 4.90 (m, 2 H), 4.75 (s, 2 H), 3.52 (s, 3 H), 3.45 (m, 1 H), 2.99 (m, 1 H), 2.62 (m, 2 H), 2.18 (m, 1 H), 1.97 (m, 2 H) | | −0.023 |
| 21 | 4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one | 415/ 417 | 6.91 (t, J = 53.4 Hz, 1 H), 4.59 (s, 2 H), 4.52 (s, 2 H), 3.26 (m, 1 H), 2.86 (m, 1 H), 2.39 (m, 3 H), 2.19 (dd, J = 16.5, 8.1 Hz, 1 H), 1.93 (dd, J = 16.5, 8.8 Hz, 1 H) | | |
| 22 | (−)-4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one | 415/ 417 | 6.91 (t, J = 53.4 Hz, 1 H), 4.59 (s, 2 H), 4.52 (s, 2 H), 3.26 (m, 1 H), 2.86 (m, 1 H), 2.39 (m, 3 H), 2.19 (dd, J = 16.5, 8.1 Hz, 1 H), 1.93 (dd, J = 16.5, 8.8 Hz, 1 H) | (73.2) | −0.156 |
| 23 | (+)-4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one | 415/ 417 | 6.91 (t, J = 53.4 Hz, 1 H), 4.59 (s, 2 H), 4.52 (s, 2 H), 3.26 (m, 1 H), 2.86 (m, 1 H), 2.39 (m, 3 H), 2.19 (dd, J = 16.5, 8.1 Hz, 1 H), 1.93 (dd, J = 16.5, 8.8 Hz, 1 H) | 73 | +0.162 |
| 24 | 4-(2-chloro-2,2-difluoroethyl)-1-({6-chloro-2-[(2,2,2-trifluoroethoxy)methyl]imidazo[2,1-b][1,3,4]thiadiazol-5-yl}methyl)pyrrolidin-2-one | 467/ 469/ 471 | 4.98 (s, 2 H), 4.77 (m, 2 H), 4.01 (q, J = 8.3 Hz, 2 H), 3.55 (m, 1 H), 3.09 (m, 1 H), 2.71 (m, 2 H), 2.46 (m, 2 H), 2.22 (m, 1 H) | | |

TABLE I-continued

Physical Characterization of Example Compounds.

| n° | IUPAC NAME | MH+ | $^1$H NMR δ (CDCl$_3$ otherwise specified) | MP° C. (DSC) | alpha$_D$ |
|---|---|---|---|---|---|
| 25 | 1-{[6-chloro-2-(methoxymethyl)imidazo[2,1-b][1,3,4]thiadiazol-5-yl]methyl}-4-(3,3,3-trifluoropropyl)pyrrolidin-2-one | 397/ 399 | (DMSO) 4.76 (s, 2 H), 4.74 (s, 2 H), 3.51 (s, 3 H), 3.45 (m, 1H), 2.94 (m, 1 H), 2.59 (m, 1 H), 2.36 (m, 1 H), 2.04 (m, 3 H), 1.65 (m, 2 H) | | |
| 26 | (−)-1-{[6-chloro-2-(methoxymethyl)imidazo[2,1-b][1,3,4]thiadiazol-5-yl]methyl}-4-(3,3,3-trifluoropropyl)pyrrolidin-2-one | 397/ 399 | (DMSO) 4.76 (s, 2 H), 4.74 (s, 2 H), 3.51 (s, 3 H), 3.45 (m, 1H), 2.94 (m, 1 H), 2.59 (m, 1 H), 2.36 (m, 1 H), 2.04 (m, 3 H), 1.65 (m, 2 H) | (59.16) | −0.034 |
| 27 | (+)-1-{[6-chloro-2-(methoxymethyl)imidazo[2,1-b][1,3,4]thiadiazol-5-yl]methyl}-4-(3,3,3-trifluoropropyl)pyrrolidin-2-one | 397/ 399 | (DMSO) 4.76 (s, 2 H), 4.74 (s, 2 H), 3.51 (s, 3 H), 3.45 (m, 1H), 2.94 (m, 1 H), 2.59 (m, 1 H), 2.36 (m, 1 H), 2.04 (m, 3 H), 1.65 (m, 2 H) | 60 | +0.049 |
| 28 | 1-{[6-chloro-2-(methoxymethyl)imidazo[2,1-b][1,3,4]thiadiazol-5-yl]methyl}-4-(2-fluoroethyl)pyrrolidin-2-one | 347/ 349 | (DMSO) 4.82 (s, 2 H), 4.64 (m, 2 H), 4.43 (m, 2 H), 3.42 (s, 3 H), 3.39 (m, 1 H), 2.97 (m, 1 H), 2.38 (m, 2 H), 2.06 (m, 1 H), 1.73 (m, 2 H) | | |
| 29 | (4R)-1-{[2-(hydroxymethyl)-6-(trifluoromethyl)imidazo[2,1-b][1,3,4]thiadiazol-5-yl]methyl}-4-(2,2,2-trifluoroethyl)pyrrolidin-2-one | 403 | (DMSO) 6.52 (s, 1 H), 4.86 (s, 2 H), 4.75 (m, 2 H), 3.40 (t, J = 8.8 Hz, 1 H), 3.03 (m, 1 H), 2.56 (m, 1 H), 2.42 (m, 3 H), 2.15 (dd, J = 16.3, 8.5 Hz, 1 H) | | +0.039 |
| 30 | (4R)-4-(2-chloro-2,2-difluoroethyl)-1-{[2-{[($^2$H$_3$)methyloxy]methyl}-6-(trifluoromethyl)imidazo[2,1-b][1,3,4]thiadiazol-5-yl]methyl}pyrrolidin-2-one | 436/ 438 | (DMSO) 4.84 (s, 2 H), 4.83 (d, J = 15.3 Hz, 1 H) 4.73 (d, J = 15.6 Hz, 1 H), 3.44 (t, J = 8.3 Hz, 1 H), 3.07 (t, J = 8.0 Hz, 1 H), 2.63 (m, 3 H), 2.43 (dd, J = 16.6, 8.3 Hz, 1 H), 2.17 (dd, J = 16.3, 8.8 Hz, 1 H) | | |
| 31 | (4R)-4-(2-chloro-2,2-difluoroethyl)-1-({2-[methoxy($^2$H$_2$)methyl]-6-(trifluoromethyl)imidazo[2,1-b][1,3,4]thiadiazol-5-yl}methyl)pyrrolidin-2-one | 435/ 437 | (DMSO) 4.83 (d, J = 15.8 Hz, 1 H), 4.73 (d, J = 15.6 Hz, 1 H), 3.43 (s, 4 H), 3.07 (t, J = 8.0 Hz, 1 H), 2.63 (m, 3 H), 2.43 (dd, J = 16.6, 8.3 Hz, 1 H), 2.17 (dd, J = 16.3, 8.5 Hz, 1 H) | | |
| 32 | (4R)-4-(2-chloro-2,2-difluoroethyl)-1-{[2-(methoxymethyl)-6-(trifluoromethyl)imidazo[2,1-b][1,3,4]thiadiazol-5-yl]($^2$H$_2$)methyl}pyrrolidin-2-one | 435/ 437 | (DMSO) 4.84 (s, 2 H), 3.45 (s, 1 H), 3.44 (s, 3 H), 3.07 (s, 1 H), 2.69-2.55 (m, 2 H), 2.63 (s, 1 H), 2.42 (m, 1 H), 2.18 (m, 1 H) | | |
| 33 | 4-(2-chloro-2,2-difluoroethyl)-1-{[2-(2-methoxyethyl)-6-(trifluoromethyl)imidazo[2,1-b][1,3,4]thiadiazol-5-yl]methyl}pyrrolidin-2-one | 447/ 449 | 4.94 (d, J = 16.0 Hz, 1 H), 4.87 (d, J = 15.2 Hz, 1 H), 3.73 (t, J = 5.5 Hz, 2 H), 3.49 (dd, J = 8.6, 8.6 Hz, 1 H), 3.41 (s, 3 H), 3.27 (t, J = 5.5 Hz, 2 H), 3.03 (dd, J = 9.9, 8.1 Hz, 1 H), 2.70 (m, 2 H), 2.45 (m, 2 H), 2.23 (dd, J = 15.8, 8.3 Hz, 1 H) | | |
| 34 | 1-{[2-(2-methoxyethyl)-6-(trifluoromethyl)imidazo[2,1-b][1,3,4]thiadiazol-5-yl]methyl}-4-(2,2,2-trifluoroethyl)pyrrolidin-2-one | 431 | 4.94 (d, J = 15.4 Hz, 1 H), 4.86 (d, J = 15.8 Hz, 1 H), 3.73 (t, J = 5.7 Hz, 2 H), 3.48 (m, 1 H), 3.41 (s, 3 H), 3.27 (t, J = 5.9 Hz, 2 H), 3.02 (m, 1 H), 2.65 (m, 2 H), 2.22 (m, 3 H) | | |
| 35 | 1-{[2-(2-methoxyethyl)-6-(trifluoromethyl)imidazo[2,1-b][1,3,4]thiadiazol-5-yl]methyl}-4-(3,3,3-trifluoropropyl)pyrrolidin-2-one | 445 | (DMSO, signals obscured by solvent) 4.76 (s, 2 H), 3.70 (t, J = 5.8 Hz, 2 H), 2.90 (dd, J = 9.3, 6.3 Hz, 1 H), 2.42 (m, 1 H), 2.24 (m, 3 H), 2.04 (dd, J = 16.3, 7.3 Hz, 1 H), 1.53 (m, 2 H) | | |

Example 9

Binding Assay to SV2A

The inhibition constant (Ki) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the $IC_{50}$. The equilibrium dissociation constant Ki is proportional to the $IC_{50}$ and is calculated using the equation of Cheng and Prusoff (Cheng Y. et al., Biochem. Pharmacol. (1972), 22, 3099-3108).

The concentration range usually encompasses 6 log units with variable steps (0.3 to 0.5 log). Assays are performed in mono- or duplicate, each Ki determination is performed on two different samples of test substance.

Cerebral cortex from 200-250 g male Sprague-Dawley rats are homogenised using a Potter S homogeniser (10 strokes at 1,000 rpm; Braun, Germany) in 20 mmol/l Tris-HCl (pH 7.4), 250 mmol/l sucrose (buffer A); all operations are performed at 4° C. The is homogenate is centrifuged at 30,000 g for 15 min. The crude membrane pellet obtained is resuspended in 50 mmol/l Tris-HCl (pH 7.4), (buffer B) and incubated 15 min at 37° C., centrifuged at 30,000 g for 15 min and washed twice with the same buffer. The final pellet is resuspended in buffer A at a protein concentration ranging from 15 to 25 mg/ml and stored in liquid nitrogen.

Membranes (150-200 μg of protein/assay) are incubated at 4° C. for 120 min in 0.5 ml of a 50 mmol/l Tris-HCl buffer (pH 7.4) containing 2 mmol/l $MgCl_2$, 1 to 2 $10^{-9}$ mol/l of [3H]-2-[4-(3-azidophenyl)-2-oxo-1-pyrrolidinyl]butanamide and increasing concentrations of the test compound of formula I. The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mol/l levetiracetam to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a p-counter (Tri-Carb 1900 or TopCount 9206, Camberra Packard, Belgium, or any other equivalent counter). Data analysis is performed by a computerized non linear curve fitting method using a set of equations describing several binding models assuming populations of independent non-interacting receptors, which obey the law of mass.

Compounds of formula I according to the invention show $pIC_{50}$ values of at least 7.0.

Example 10

Binding Assay to SV2C

For this assay, SV2C expressed in COS-7 cells are used under standard conditions (see Example 6). [$^3$H]-(+)-4-(3-azido-2,4-difluorophenyl)-1-(1H-imidazol-1-ylmethyl)pyrrolidin-2-one is the used as the radio ligand that binds selectively to SV2C whereby the differential binding of the test compounds is measured, the $IC_{50}$s of the test compounds are calculated under conditions known to a person skilled in the art.

Compounds of formula I according to the invention show $pIC_{50}$ values of at least 6.5.

Example 11

Seizure Models

The following 3 seizure models are viewed to be predictive in the assessment of compounds that are potentially useful in the control of seizures in patients with epilepsy. In addition, the 6 Hz seizure model has been proposed to be useful for identification of compounds possessing clinical activity in patients with refractory seizures (Barton et al., Epilepsy Res. (2001), 47, 217-27).

11.1 Animal Model of Sound-Susceptible Mice (Audiogenic Seizures)

The objective of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41).

Male or female genetically sound-sensitive mice (14-28 g; N=10), derived from a DBA strain originally selected by Dr. Lehmann of the Laboratory of Acoustic Physiology (Paris) and bred in the UCB Pharma Sector husbandry unit since 1978, are used. The experimental design consisted of several groups, one group receiving the vehicle control and the other groups different doses of the test-compound. The compounds are administered intraperitoneally 60 minutes before the induction of audiogenic seizures. The range of the doses administered had a logarithmic progression, generally between $1.0 \times 10$-5 mol/kg and $1.0 \times 10$-3 mol/kg, but lower or higher doses are tested if necessary.

For testing, the animals are placed in small cages, one mouse per cage, in a sound-attenuated chamber. After a period of orientation of 30 seconds, the acoustic stimulus (90 dB, 10-20 kHz) is delivered for 30 seconds via loudspeakers positioned above each cage. During this interval, the mice are observed and the presence of the 3 phases of the seizure activity namely wild running, clonic and tonic convulsions, is recorded. The proportion of mice protected against wild running, clonic and tonic convulsions, respectively, is calculated.

For active compounds, an ED50 value, i.e. the dose producing 50% protection relative to the control group, together with 95% confidence limits, is calculated using a Probit Analysis (SAS/STAT® Software, version 6.09, PROBIT procedure) of the proportions of protected mice for each of the 3 phases of the seizure activity.

Compounds synthesized according to the procedure described in examples 1 to 5 and described in table 1 are tested in the audiogenic seizure in mice, according to the procedure described above, and are found active.

11.2 6 Hz Seizure Model

Male NMRI mice (Charles River, France) weighing 20-30 g are used in all experiments. The animals are kept on a 12/12-h light/dark cycle with lights on at 0600 h and are housed at a temperature maintained at 20-21° C. and at humidity of about 40%. The mice are housed in groups of 10 per cage (38×26×14 cm). All animals have free access to standard pellet food and water before random assignment to experimental groups consisting of 10 mice each. All animal experiments are done according to the Helsinki declaration and conducted in accordance with the guidelines of the European Community Council directive 86/609/EEC. A local ethical committee approved the experimental protocol.

The 6 Hz model is carried out according to a previously described protocol (Kaminski et al., Epilepsia (2004), 45, 864-867). Briefly, corneal stimulation (44 mA, 0.2 ms-duration monopolar rectangular pulses at 6 Hz for 3 s) is delivered by a constant-current device (ECT Unit 57800; Ugo Basile, Comerio, Italy). A drop of 0.4% oxybuprocaine hydrochloride (Unicaine, Thea, France) is placed on the eyes before electrical stimulation. During the stimulation, mice are manually restrained and released into the observation cage (38× 26×14 cm) immediately after the current application. The seizures are often preceded by a brief period (~2-3 s) of intense locomotor agitation (wild running and jumping). The animals then exhibit a "stunned" posture associated with rearing, forelimb automatic movements and clonus, twitching of the vibrissae, and Strub-tail. At the end of the seizure, animals resume their normal exploratory behavior. The experimental endpoint is protection against the seizure. The animal is considered to be protected if it resumes its normal exploratory behavior within 7 s from the stimulation.

In vivo activities determined for test compounds are comprised between 0.05 mg/kg and 10 mg/kg.

11.3 Pentylenetetrazol (PTZ) seizure model

Animals are prepared as described in example 11.2.

Pentylenetetrazol is used at the previously established CD97 dose of 89 mg/kg; a convulsive dose inducing clonic convulsions of all four extremities in 97% of mice (Klitgaard et al., Eur. J. Pharmacol. (1998), 353, 191-206). Immediately following pentylenetetrazol injection the mice are placed individually in Perspex cages and observed for the presence of clonic convulsions in all four extremities and tonic hind-limb extension during 60 min period.

The invention claimed is:

1. A 2-oxo-1-pyrrolidinyl imidazothiadiazole derivative in the form of formula I or the form of an enantiomer, diastereomer or mixture, or pharmaceutically acceptable salt thereof,

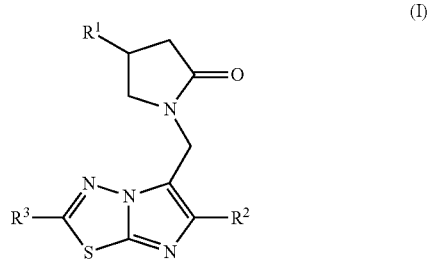

(I)

wherein
$R^1$ is a $C_{1-4}$ alkyl containing at least one halogen substituent;
$R^2$ is either a halogen or a $C_{1-4}$ alkyl containing at least one halogen substituent;
$R^3$ is a $C_{1-4}$ alkyl containing at least one hydroxy or alkoxy substituent.

2. The compound according to claim 1, wherein $R^1$ is a 2,2-difluoropropyl, a 2-chloro-2,2-difluoroethyl, a 2,2-difluoroethyl, a 2,2,2-trifluoroethyl, a 3,3,3-trifluoropropyl or a 2-fluoroethyl moiety.

3. The compound according to claim 1, wherein $R^2$ is either a chloro, a difluoromethyl or a trifluoromethyl moiety.

4. The compound according to claim 1, wherein $R^3$ is either a hydroxymethyl, a methoxymethyl, a [($^2H_3$)methyloxy]methyl, a methoxy($^2H_2$)methyl, a (2,2,2-trifluoroethoxy)methyl or a 2-methoxyethyl moiety.

5. The compound according to claim 1, wherein
$R^1$ is a 2,2-difluoropropyl, a 2-chloro-2,2-difluoroethyl, a 2,2,2-trifluoroethyl or a 3,3,3-trifluoropropyl moiety;
$R^2$ is a chloro, a difluoromethyl or a trifluoromethyl moiety; and
$R^3$ is a methoxymethyl moiety.

6. The compound according to claim 1 selected from the group consisting of:
4-(2,2-difluoropropyl)-1-{[2-(methoxymethyl)-6-(trifluoromethyl)imidazo[2,1-b][1,3,4]thiadiazol-5-yl]methyl}pyrrolidin-2-one;
(+)-4-(2,2-difluoropropyl)-1-{[2-(methoxymethyl)-6-(trifluoromethyl)imidazo[2,1-b][1,3,4]thiadiazol-5-yl]methyl}pyrrolidin-2-one;
(−)-4-(2,2-difluoropropyl)-1-{[2-(methoxymethyl)-6-(trifluoromethyl)imidazo[2,1-b][1,3,4]thiadiazol-5-yl]methyl}pyrrolidin-2-one;
4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one trifluoroacetate;
(4S)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one;
(4R)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one;
4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one;
(4R)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one;
(4S)-4-(2-chloro-2,2-difluoroethyl)-1-{[2-(hydroxymethyl)-6-(trifluoromethyl)imidazo[2,1-b][1,3,4]thiadiazol-5-yl]methyl}pyrrolidin-2-one;
1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one;
(4R)-1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one;
(4S)-1-{[2-(methoxymethyl)-6-(trifluoromethyl)imidazo[2,1-b][1,3,4]thiadiazol-5-yl]methyl}-4-(2,2,2-trifluoroethyl)pyrrolidin-2-one;
1-{[2-(hydroxymethyl)-6-(trifluoromethyl)imidazo[2,1-b][1,3,4]thiadiazol-5-yl]methyl}-4-(2,2,2-trifluoroethyl)pyrrolidin-2-one;
1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one;
(4S)- 1-{[2-(methoxymethyl)-6-(trifluoromethyl)imidazo[2,1-b][1,3,4]thiadiazol-5-yl]methyl}-4-(3,3,3-trifluoropropyl)pyrrolidin-2-one;
(4R)- 1-{[2-(methoxymethyl)-6-(trifluoromethyl)imidazo[2,1-b][1,3,4]thiadiazol-5 -yl]methyl}-4-(3,3,3-trifluoropropyl)pyrrolidin-2-one;
(4S)-1-{[2-(hydroxymethyl)-6-(trifluoromethyl)imidazo[2,1-b][1,3,4]thiadiazol-5-yl]methyl}-4-(3,3,3-trifluoropropyl)pyrrolidin-2-one;
4-(2,2-difluoroethyl)-1- {[2-(methoxymethyl)-6-(trifluoromethyl)imidazo[2,1-b][1,3,4]thiadiazol-5-yl]methyl}pyrrolidin-2-one;

(+)-4-(2,2-difluoroethyl)-1-{[2-(methoxymethyl)-6-(trifluoromethyl)imidazo[2,1-b][1,3,4]thiadiazol-5-yl]methyl}pyrrolidin-2-one, isomer A;

(−)-4-(2,2-difluoroethyl)-1-{[2-(methoxymethyl)-6-(trifluoromethyl)imidazo[2,1-b][1,3,4]thiadiazol-5-yl]methyl}pyrrolidin-2-one, isomer B;

4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one;

(−)-4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one;

(+)-4-(2-chloro-2,2-difluoroethyl)-1-{[6-(difluoromethyl)-2-(methoxymethyl)imidazo[2,1-b][1,3,4]thiadiazol-5-yl]methyl}pyrrolidin-2-one;

4-(2-chloro-2,2-difluoroethyl)-1-({6-chloro-2-[(2,2,2-trifluoroethoxy)methyl]imidazo[2,1-b][1,3,4]thiadiazol-5-yl}methyl)pyrrolidin-2-one;

1-{[6-chloro-2-(methoxymethyl)imidazo[2,1-b][1,3,4]thiadiazol-5-yl]methyl}-4-(3,3,3-trifluoropropyl)pyrrolidin-2-one;

(−)-1-{[6-chloro-2-(methoxymethyl)imidazo[2,1-b][1,3,4]thiadiazol-5-yl]methyl}-4-(3,3,3-trifluoropropyl)pyrrolidin-2-one;

(+)-1-{[6-chloro-2-(methoxymethyl)imidazo[2,1-b][1,3,4]thiadiazol-5-yl]methyl}-4-(3,3,3-trifluoropropyl)pyrrolidin-2-one;

1-{[6-chloro-2-(methoxymethyl)imidazo[2,1-b][1,3,4]thiadiazol-5-yl]methyl}-4-(2-fluoroethyl)pyrrolidin-2-one;

(4R)-1-{[2-(hydroxymethyl)-6-(trifluoromethyl)imidazo[2,1-b][1,3,4]thiadiazol-5-yl]methyl}-4-(2,2,2-trifluoroethyl)pyrrolidin-2-one;

(4R)-4-(2-chloro-2,2-difluoroethyl)-1-{[2-{[($^2$H$_3$)methyloxy]methyl}-6-(trifluoromethyl)imidazo[2,1-b][1,3,4]thiadiazol-5-yl]methyl}pyrrolidin-2-one;

(4R)-4-(2-chloro-2,2-difluoroethyl)-1-({2-[methoxy($^2$H$_2$)methyl]-6-(trifluoromethyl)imidazo[2,1-b][1,3,4]thiadiazol-5-yl}methyl)pyrrolidin-2-one;

(4R)-4-(2-chloro-2,2-difluoroethyl)-1-{[2-(methoxymethyl)-6-(trifluoromethyl)-imidazo[2,1-b][1,3,4]thiadiazol-5-yl](2H2)methyl}pyrrolidin-2-one 4-(2-chloro-2,2-difluoroethyl)-1-{[2-(2-methoxyethyl)-6-(trifluoromethyl)imidazo[2,1-b][1,3,4]thiadiazol-5-yl]methyl}pyrrolidin-2-one;

1-{[2-(2-methoxyethyl)-6-(trifluoromethyl)imidazo[2,1-b][1,3,4]thiadiazol-5-yl]methyl}-4-(2,2,2-trifluoroethyl)pyrrolidin-2-one; and 1-{[2-(2-methoxyethyl)-6-(trifluoromethyl)imidazo[2,1-b][1,3,4]thiadiazol-5-yl]methyl}-4-(3,3,3-trifluoropropyl)pyrrolidin-2-one.

7. A pharmaceutical composition comprising a compound according to claim 1 in combination with a pharmaceutically acceptable diluent or carrier.

8. The compound according to claim 2, wherein $R^2$ is a chloro, a difluoromethyl or a trifluoromethyl moiety.

9. The compound according to claim 2, wherein $R^3$ is a hydroxymethyl, a methoxymethyl, a [($^2$H$_3$)methyloxy]methyl, a methoxy($^2$H$_2$) methyl, a (2,2,2-trifluoroethoxy)methyl or a 2-methoxyethyl moiety.

10. The compound according to claim 8, wherein $R^3$ is a hydroxymethyl, a methoxymethyl, a [($^2$H$_3$)methyloxy]methyl, a methoxy($^2$H$_2$) methyl, a (2,2,2-trifluoroethoxy)methyl or a 2-methoxyethyl moiety.

11. A pharmaceutical composition comprising a compound according to claim 2 in combination with a pharmaceutically acceptable diluent or carrier.

12. A pharmaceutical composition comprising a compound according to claim 3 in combination with a pharmaceutically acceptable diluent or carrier.

13. A pharmaceutical composition comprising a compound according to claim 5 in combination with a pharmaceutically acceptable diluent or carrier.

14. A pharmaceutical composition comprising a compound according to claim 6 in combination with a pharmaceutically acceptable diluent or carrier.

15. A method of treating a patient with refractory epilepsy, the method comprising administering to the patient an effective amount of a compound according to claim 1, optionally together with a pharmaceutically acceptable diluent or carrier.

16. A method of treating a patient with refractory epilepsy, the method comprising administering to the patient an effective amount of a compound according to claim 2, optionally together with a pharmaceutically acceptable diluent or carrier.

17. A method of treating a patient with refractory epilepsy, the method comprising administering to the patient an effective amount of a compound according to claim 3, optionally together with a pharmaceutically acceptable diluent or carrier.

18. A method of treating a patient with refractory epilepsy, the method comprising administering to the patient an effective amount of a compound according to claim 5, optionally together with a pharmaceutically acceptable diluent or carrier.

19. A method of treating a patient with refractory epilepsy, the method comprising administering to the patient an effective amount of a compound according to claim 6, optionally together with a pharmaceutically acceptable diluent or carrier.

20. The compound according to claim 1 which is (4R)-4-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one.

\* \* \* \* \*